United States Patent
Gorman et al.

(10) Patent No.: US 7,144,384 B2
(45) Date of Patent: Dec. 5, 2006

(54) DISPENSER COMPONENTS AND METHODS FOR PATIENT INFUSION DEVICE

(75) Inventors: William Gorman, South Hamilton, MA (US); John T. Garibotto, Charlestown, MA (US); J. Christopher Flaherty, Topsfield, MA (US); John R. Bussiere, Littleton, MA (US); Gaurav Rohatgi, Franklin, MA (US)

(73) Assignee: Insulet Corporation, Bedford, MA (US)

( * ) Notice: Subject to any disclaimer, the term of this patent is extended or adjusted under 35 U.S.C. 154(b) by 163 days.

(21) Appl. No.: 10/261,003

(22) Filed: Sep. 30, 2002

(65) Prior Publication Data

US 2004/0064088 A1    Apr. 1, 2004

(51) Int. Cl.
*A61M 37/00* (2006.01)
(52) U.S. Cl. .................................. 604/131; 604/151
(58) Field of Classification Search .............. 604/150, 604/151, 152, 154, 156, 30, 131, 236, 247; 128/DIG. 1
See application file for complete search history.

(56) References Cited

U.S. PATENT DOCUMENTS

| | | |
|---|---|---|
| 3,631,847 A | 1/1972 | Hobbs |
| 3,812,843 A | 5/1974 | Wootten et al. |
| 3,885,662 A | 5/1975 | Schaefer |
| 4,067,000 A | 1/1978 | Carlson |
| 4,108,177 A | 8/1978 | Pistor |
| 4,151,845 A | 5/1979 | Clemens |
| 4,193,397 A | 3/1980 | Tucker et al. |
| 4,211,998 A | 7/1980 | Junginger et al. |
| 4,231,019 A | 10/1980 | Junginger et al. |
| 4,268,150 A | 5/1981 | Chen |
| 4,342,311 A | 8/1982 | Whitney et al. |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |

(Continued)

FOREIGN PATENT DOCUMENTS

DE    4200595    7/1993

(Continued)

OTHER PUBLICATIONS

Web-Site Brochure dated Jan. 4, 2000. MiniMed 508. "Doing its job. Naturally." www.minimed.com/tiles/mm_113.htm.

(Continued)

*Primary Examiner*—Sharon Kennedy

(57) ABSTRACT

A device for delivering fluid to a patient including an exit port assembly, a reservoir including a side wall extending towards an outlet connected to the exit port assembly, a threaded lead screw received at least partly in the reservoir and longitudinally extending towards the outlet, and a plunger secured to the lead screw and having an outer periphery linearly slideable along the side wall of the reservoir. A tube is coaxially received on the lead screw and includes a longitudinal slot, a pin extending through the lead screw and the slot of the tube, and a gear is secured to the tube for rotation therewith.

107 Claims, 20 Drawing Sheets

U.S. PATENT DOCUMENTS

| | | |
|---|---|---|
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,836,752 A | 6/1989 | Burkett |
| D303,013 S | 8/1989 | Konopka |
| 4,855,746 A | 8/1989 | Stacy |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| D306,691 S | 3/1990 | Arai |
| 4,944,659 A | 7/1990 | Labbe et al. |
| D311,735 S | 10/1990 | Arai et al. |
| 4,969,874 A | 11/1990 | Michel et al. |
| 4,973,998 A | 11/1990 | Gates |
| D315,727 S | 3/1991 | Arai et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,125,415 A | 6/1992 | Bell |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Böcker et al. |
| 5,514,096 A | 5/1996 | Hiejima |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,678,539 A | 10/1997 | Schubert et al. |
| 5,685,859 A | 11/1997 | Kornerup |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| 5,858,239 A | 1/1999 | Kenley |
| D405,524 S | 2/1999 | Falk et al. |
| 5,865,806 A | 2/1999 | Howell |
| 5,871,470 A | 2/1999 | McWha |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,957,895 A | 9/1999 | Sage et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |
| 6,206,850 B1 | 3/2001 | O'Neil |
| 6,244,776 B1 | 6/2001 | Wiley |
| 6,363,609 B1 | 4/2002 | Pickren |
| 6,375,638 B1 | 4/2002 | Nason et al. |
| 6,520,936 B1 | 2/2003 | Mann |
| 6,527,744 B1 | 3/2003 | Kriesel et al. |
| 6,572,585 B1 | 6/2003 | Choi |
| 6,656,158 B1 | 12/2003 | Mahoney et al. |
| 6,656,159 B1 | 12/2003 | Flaherty |
| 6,692,457 B1 | 2/2004 | Flaherty |
| 6,723,072 B1 | 4/2004 | Flaherty et al. |
| 6,740,059 B1 | 5/2004 | Flaherty |
| 2004/0068224 A1 | 4/2004 | Couvillon |

FOREIGN PATENT DOCUMENTS

| | | |
|---|---|---|
| DE | 19920896 | 9/2000 |

| | | |
|---|---|---|
| EP | 0342947 | 5/1989 |
| EP | 0319272 | 6/1989 |
| EP | 0763369 | 3/1997 |
| EP | 0867196 | 3/1998 |
| EP | 0867196 | 9/1998 |
| EP | 0937475 | 8/1999 |
| EP | 1177802 A1 | 2/2002 |
| WO | WO81/01658 | 6/1981 |
| WO | WO-81/01658 | 6/1981 |
| WO | WO86/06796 | 11/1986 |
| WO | WO-8606796 | 11/1986 |
| WO | WO98/00193 | 1/1998 |
| WO | WO98/01071 | 1/1998 |
| WO | WO-98/01071 | 1/1998 |
| WO | WO-9800193 | 1/1998 |
| WO | WO-98/41267 | 9/1998 |
| WO | WO99/10040 | 3/1999 |
| WO | WO-99/10049 | 3/1999 |
| WO | WO00/19887 | 9/1999 |
| WO | WO99/56803 | 11/1999 |
| WO | WO-99/56803 | 11/1999 |
| WO | WO99/62576 | 12/1999 |
| WO | WO-99/62576 | 12/1999 |
| WO | WO-00/10628 | 3/2000 |
| WO | WO-00/13580 | 3/2000 |
| WO | WO0010628 | 3/2000 |
| WO | WO-00/19887 | 4/2000 |
| WO | WO00/29047 | 5/2000 |
| WO | WO00/29049 | 5/2000 |
| WO | WO-00/29049 | 5/2000 |
| WO | WO00/74752 | 5/2000 |
| WO | WO-0029047 | 5/2000 |
| WO | WO00/30705 | 6/2000 |
| WO | WO00/78210 | 6/2000 |
| WO | WO-0030705 | 6/2000 |
| WO | WO-00/48112 | 8/2000 |
| WO | WO00/48112 | 8/2000 |
| WO | WO00/61215 | 10/2000 |
| WO | WO-00/61215 | 10/2000 |
| WO | WO01/52727 | 1/2001 |
| WO | WO-01/52727 | 7/2001 |
| WO | WO01/5663 | 8/2001 |
| WO | WO-01/56633 | 8/2001 |
| WO | WO01/76684 | 10/2001 |
| WO | WO-01/76684 | 10/2001 |
| WO | WO-02/20073 | 3/2002 |
| WO | WO02/20073 | 3/2002 |
| WO | WO02/26282 | 4/2002 |
| WO | WO-02/26282 | 4/2002 |

OTHER PUBLICATIONS

Web-Site Brochure dated Dec. 20, 1999. Applied Medical Technology. "508 Pump Information". www.applied-medical.co.uk/508.htm.
Web-Site Brochure dated Jan. 4, 2000. "The Glucose Sensor". www.animascorp.com/sensor_f.html.
Web-Site Brochure dated Dec. 20, 1999, "The Animas R-1000 Insulin Pump". www.animascorp.com/pump_f_s.html.
Web-Site Brochure dated Dec. 20, 1999. "The Animas R-1000 Insulin Pump". www.animascorp.com/pump_f_f.html.
Web-Site Brochure dated Jan. 4, 2000. SOOIL-Homepage. "Portable Insulin Pump". www.sooil.com/intro2.htm.
Web-Site Brochure dated Jan. 4, 2000. SOOIL-Homepage. "Portable Insulin Pump". www.sooil.com/product2.htm.
Web-Site Brochure dated Jan. 4, 2000. SOOIL-Homepage. "Portable Insulin Pump". www.sooil.com/product3.htm.
Web-Site Brochure dated Jan. 4, 2000. SOOIL-Homepage. "Portable Insulin Pump". www.sooil.com/product4.htm.
US 5,954,699, Dec. 1999, Jost et al (withdrawn).
"Communication Pursuant to Article 96(2) EPC EPA No. 01968320.0". (Jan. 21, 2005).
"Communication Pursuant To Article 96(2) EPC EPA No. 01977472.8", (Jul. 19, 2004).
"Communication Pursuant to Article 96(2) EPC EPA No. 01987579.8", (Jan. 26, 2005).
"Examiner's First Report On US Patent Publication No. 2001288575", (Mar. 25, 2005).
"Examiner's First Report On Patent Application No. 2001296588", (Mar. 16, 2005).
"Examiner's First Report On Patent Application No. 2002239709", (May 18, 2005).
"International Preliminary Examination Report PCT/US03/03731", (Jun. 17, 2004).
"International preliminary Examination PCT/US01/31089", (Feb. 5, 2004).
"International Preliminary Examination Report PCT/US01/10933", (Oct. 28, 2003).
"International Preliminary Examination Report PCT/US01/27108", (Nov. 4, 2003).
"International Preliminary Examination Report PCT/US02/05338", (Apr. 3, 2003).
"International Preliminary Examination Report PCT/US02/28053", (Dec. 9, 2004).
"International Preliminary Examination Report PCT/US03/09606", (Dec. 6, 2003).
"International Preliminary Examination Report PCT/US03/09952", (Jan. 20, 2004).
"International Preliminary Examination Report PCT/US03/12370", (Feb. 11, 2004).
"International Preliminary Examination Report PCT/US03/16545", (Feb. 23, 2004).
"International Preliminary Examination Report PCT/US03/28769", (Aug. 12, 2004).
"International Search Report PCT/US/03/16640", (Oct. 2, 2003).
"International Search Report PCT/US01/51285", (Aug. 2, 2004).
"International Search Report PCT/US03/29019", (Aug. 2, 2004).
"Written Opinion PCT US/02/30803", (Aug. 26, 2003).
"Written Opinion PCT/US03/19756", (Aug. 6, 2004).

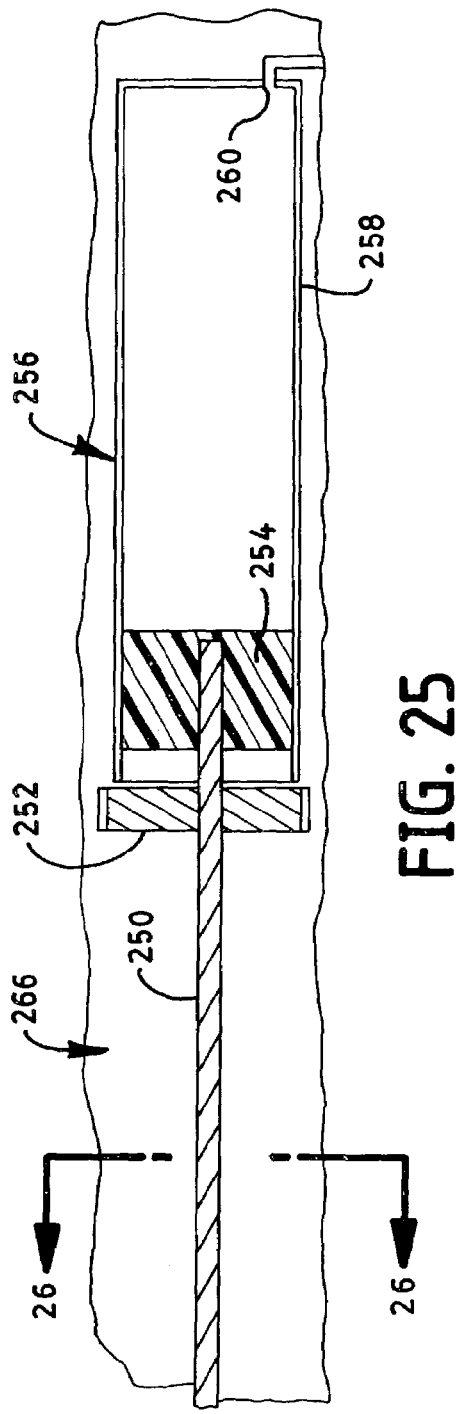
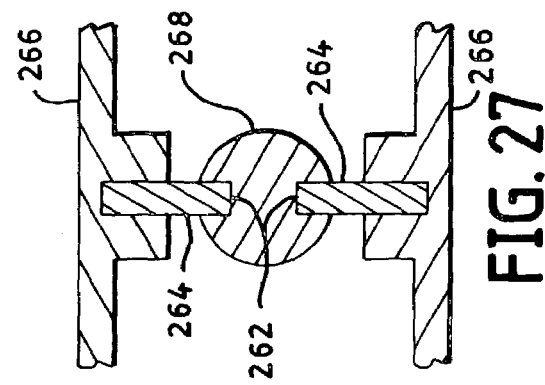

DISPENSER COMPONENTS AND METHODS FOR PATIENT INFUSION DEVICE

CROSS-REFERENCE TO RELATED APPLICATIONS

INFUSION, which is assigned to the assignee of the present application, and is incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids such as insulin to a mammalian patient. Even more particularly, the present invention is directed to various new and improved dispenser components and methods for an infusion device.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge, a syringe or an IV bag, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, lightweight, easy-to-use alternative for parenteral delivery of liquid medicines.

In response, the applicant of the present application provided a small, low cost, light-weight, easy-to-use device for delivering liquid medicines to a patient. The device, which is described in detail in U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor. What is still desired, however, are additional new and improved components and methods for devices for delivering fluid to a patient.

SUMMARY OF THE INVENTION

The present invention provides a device for delivering fluid to a patient. The device includes an exit port assembly, a reservoir including a side wall extending towards an outlet connected to the exit port assembly, a threaded lead screw received at least partly in the reservoir and longitudinally extending towards the outlet, and a plunger secured to the lead screw. The plunger has an outer periphery longitudinally slideable along the side wall of the reservoir so that longitudinal movement of the lead screw causes fluid to be forced out of the outlet to the exit port assembly. A tube is coaxially received on the lead screw and includes a longitudinal slot, and a pin extends through the lead screw and the slot of the tube such that the lead screw rotates with the tube. A gear having radially extending teeth is secured to the tube for rotation therewith.

According to one aspect of the present invention, the device further includes a reference element secured to the pin, at least one light emitter directed laterally at the tube for directing a beam of light at the tube, and at least one light detector directed laterally at the tube for receiving the beam of light reflected away from the tube. One of the tube and the reference element has a light reflective outer surface, so that the detector provides a signal upon movement of the reference element past the detector. In this manner, longitudinal movement of the lead screw is monitored. According to one aspect, the reference element has a light reflective outer surface. According to another aspect, the reference element is annular and coaxially received for sliding movement along an outer surface of the tube.

According to a further aspect of the present invention, a processor is connected to the light detector and is programmed to apply a charge to the shape memory element and remove the charge upon receiving a signal from the light detector indicative of a desired amount of linear movement of the lead screw. In this manner, power is applied to the shape memory element only for as long as needed to cause movement of the lead screw as desired.

According to an additional aspect of the present invention, the lead screw extends through and is threadedly received within a nut assembly that is non-rotating with respect to the lead screw, and is linearly fixed in position with respect to the reservoir. Upon rotation of the lead screw, therefore, the lead screw moves longitudinally through and with respect to the nut assembly. According to a further aspect, the nut assembly includes at least two laterally movable threaded inserts including threaded surfaces for threadedly receiving the lead screw upon being biased laterally inwardly against the lead screw, a spring biasing the threaded inserts laterally inwardly against the lead screw, and at least one spacer cam movable between a first position preventing the threaded inserts from being biased laterally inwardly against the lead screw and a second position allowing the threaded inserts to be biased laterally inwardly against the lead screw.

According to another aspect of the present invention, the fluid delivery device also includes a set of at least two pawls, wherein each pawl engages teeth of the gear and allows rotation of the gear in a single direction. The pawls allow rotation of the gear, and the tube and the lead screw, in a single direction. Among other features and benefits, the deployment of at least two pawls provides redundancy in case one of the pawls snaps or otherwise fails during operation of the device.

According to yet another aspect of the present invention, the device includes a ratchet member movable with respect to the gear and including a ratchet engaging teeth of the gear such that movement of the ratchet in a first direction causes rotation of the gear while movement of the ratchet in a second direction causes no rotation of the gear. An elongated shape memory element is secured to the ratchet member. The shape memory element has a changeable length decreasing from an uncharged length to a charged length when at least one charge is applied to the shape memory element and is arranged with the ratchet member such that the changeable length of the shape memory element decreasing from an uncharged length to a charged length causes movement of the ratchet in one of the first and the second directions.

According to one aspect, the shape memory element is arranged such that the changeable length of the shape memory element decreasing from an uncharged length to a charged length causes movement of the ratchet in the first direction. According to a further aspect, the ratchet member includes at least one anchor fixed in position with respect to the gear, and at least one spring biasing the ratchet in the second direction and away from the anchor. The springs comprise bent portions of flat sheet material. The ratchet is connected to the springs through a flat extension portion, which also is biased away from the anchors by the springs.

According to yet a further aspect of the present invention, a first electrical lead is connected to the gear, a second electrical lead is connected to the ratchet, and a third electrical lead is connected to the pawl. In addition, the gear, the ratchet, and the pawls are made from electrically conductive material. A processor is connected to the first, the second and the third electrical leads and is programmed to determine whether the gear has been rotated based at least in part on electrical discontinuities between the ratchet, the gear, and the pawl. According to another aspect, the processor is programmed to apply a charge to the shape memory element and remove the charge upon sensing a predetermined number of electrical discontinuities among the electrical leads. In this manner, power is applied to the shape memory element only for as long as needed to cause movement of the lead screw as desired.

According to another aspect of the present invention, an electrically conductive brush is biased against a face of the gear, and the face of the gear includes radially spaced bumps thereon. One of the face and the bumps are electrically conductive, and the brush is connected to a processor, which is programmed to determine whether the gear has rotated based at least in part on electrical discontinuities between the brush and the gear.

According to an additional aspect of the present invention, an encoder disk is coaxially secured to the tube and includes radially spaced light reflective indicia thereon. A light emitter and a light detector are directed at the encoder disk and connected to a processor, which is programmed to determine the amount of rotation of the tube based upon movement of the radially spaced light reflective indicia of the encoder disk.

According to one aspect of the present invention, the lead screw extends through a fixed, non-rotatable nut, a rotary motor is mated to a proximal end of the lead screw for causing rotation of the lead screw relative to the motor, and a longitudinal guide extends parallel with the lead screw and receives the motor. The guide allows longitudinal movement of the motor and prevents rotation of the motor, so that actuation of the motor causes longitudinal movement of the lead screw through the fixed nut. According to another aspect, the rotary motor and the longitudinal guide have non-circular cross-sections preventing rotation of the motor with respect to the guide.

According to an additional aspect of the present invention, a reflector is secured for longitudinal movement with the lead screw, at least one light emitter is fixed with respect to the lead screw and directed longitudinally at the reflector, and at least one light detector is fixed with respect to the lead screw and directed longitudinally at the reflector. According to one aspect, the reflector is oriented at an angle with respect to the guide of the motor. A processor is connected to the light emitter and the light detector and programmed to determine a longitudinal distance of the reflector from the light emitter based upon a lateral distance between a beam of light directed from the light emitter to the reflector and the beam of light as received by the light detector from the reflector. According to another aspect, the reflector is secured to the motor.

According to yet another aspect of the present invention, at least one light emitter is directed laterally within the longitudinal guide, at least one light detector is directed laterally within the longitudinal guide, and one of the guide and the motor is relatively light reflective. In this manner, the light detector can provide a signal indicative of longitudinal movement of the motor with the lead screw and within the longitudinal guide.

According to yet another aspect of the present invention, the lead screw is made from electrically resistive material and the fixed nut is made from electrically conductive material. A processor is connected to the nut and the lead screw and programmed to detect an electrical signal between the nut and the lead screw. The processor is further programmed to determine a relative longitudinal position between the nut and the lead screw based on one of the electrical signal and changes to the electrical signal.

According to still an additional aspect of the present invention, the device further includes teeth secured to the tube and a pawl engaging the teeth of the tube and allowing rotation of the tube in a single direction. The teeth can be unitarily formed with the tube in order to simplify manufacturing.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 25 is a top plan view of an exemplary embodiment of a lead screw, a plunger a reservoir, and a housing portion constructed in accordance with the present invention, for use with a fluid delivery device;

FIG. 26 is a sectional view of the lead screw and the housing portion taken along line 26—26 of FIG. 25;

FIG. 27 is a sectional view of another exemplary embodiment of a lead screw and corresponding housing portions constructed in accordance with the present invention.

Like reference characters designate identical or corresponding components and units throughout the several views.

DETAILED DESCRIPTION OF THE EXEMPLARY EMBODIMENTS

Figure 1:
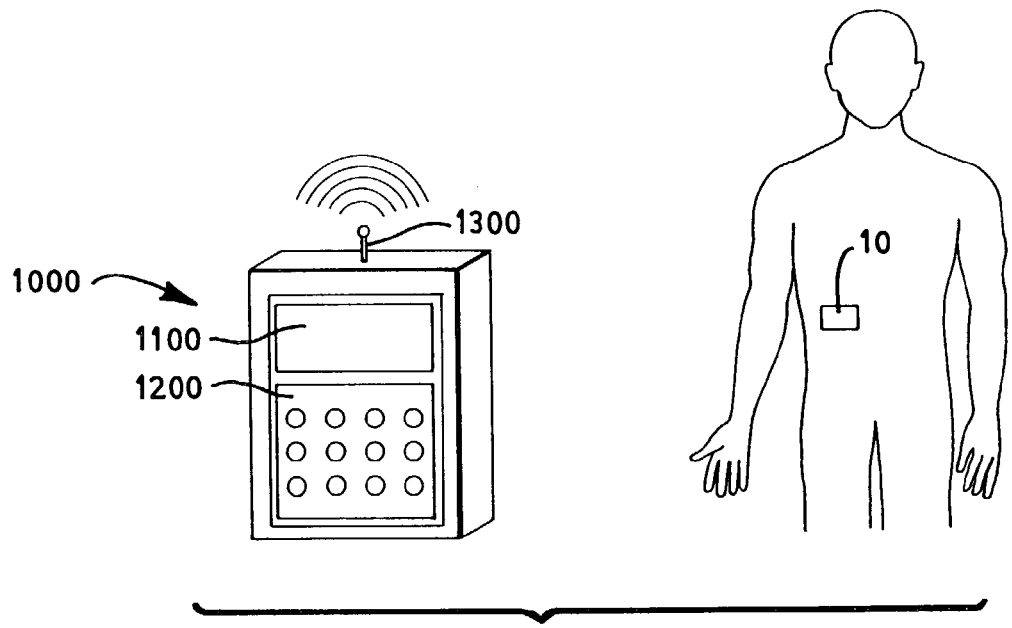
FIG. 1 is a perspective view of a first exemplary embodiment of a fluid delivery device constructed in accordance with the present invention and shown secured on a patient, and a remote control device for use with the fluid delivery device (the remote control device being enlarged with respect to the patient and the fluid delivery device for purposes of illustration)
Figure 2A:
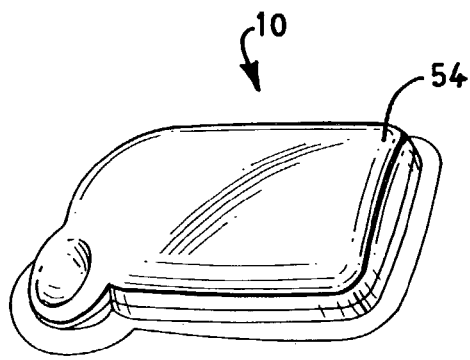
FIGS. 2a and 2b are enlarged top and bottom perspective views, respectively, of the fluid delivery device of FIG. 1.
Figure 2B:
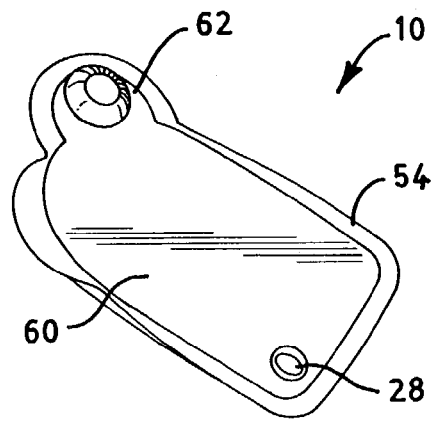
Figure 3:
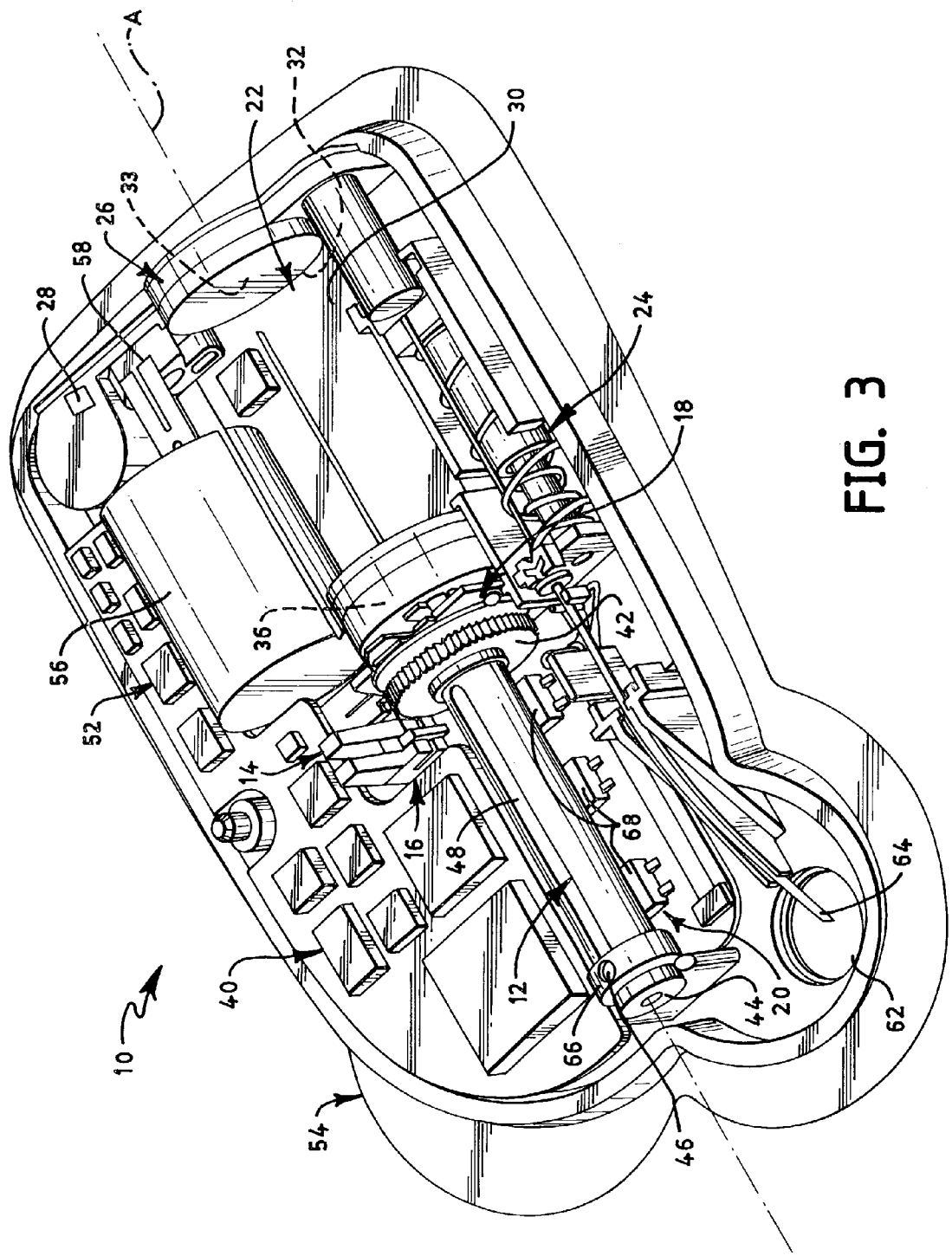
FIG. 3 is a further enlarged top perspective view of the fluid delivery device of FIG. 1, shown with a top housing portion removed to reveal interior portions of the fluid delivery device, including an exemplary embodiment of a lead screw assembly constructed in accordance with the present invention.

Referring to FIGS. 1 through 3, there is illustrated an exemplary embodiment of a fluid delivery device 10 constructed in accordance with the present inventions. Referring to FIG. 3, the fluid delivery device 10 includes exemplary embodiments of a lead screw assembly 12, a ratchet member 14 for turning the lead screw assembly 12, a set of pawls 16 for allowing rotation of the lead screw assembly 12 in a single direction, a fixed nut assembly 18 engaging the lead screw assembly 12, and a sensor assembly 20 for monitoring longitudinal movement of the lead screw assembly 12. All of these exemplary embodiments are constructed in accordance with the present invention.

Referring to FIG. 3, the fluid delivery device 10 also includes exemplary embodiments of a reservoir 22 for receiving and holding fluid to be delivered by the device 10, a transcutaneous access tool 24 for providing fluid communication between the reservoir 22 and a patient, and a laminated flow path assembly 26 connecting a fill port 28 to the reservoir 22 and the reservoir 22 to the transcutaneous access tool 24. These components are described in detail in U.S. application Ser. No. 10/260,192, filed on the same day as the present application, which is assigned to the assignee of the present application, and has previously been incorporated herein by reference.

The fluid delivery device 10 can be used for the delivery of fluids to a person or animal. The types of liquids that can be delivered by the fluid delivery device 10 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device 10 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. The volume of the reservoir 22 is chosen to best suit the therapeutic application of the fluid delivery device 10 impacted by such factors as available concentrations of medicinal fluids to be delivered, acceptable times between refills or disposal of the fluid delivery device 10, size constraints and other factors.

In the exemplary embodiment shown in FIG. 3, the reservoir 22 includes a cylindrical side wall 30 extending towards an outlet 32 connected to the transcutaneous access tool 24. The lead screw assembly 12 includes a threaded lead screw 34 received in the reservoir 22 and extending towards the outlet 32 of the reservoir 22 generally parallel with the side wall 30 of the reservoir 22. A plunger 36 is secured to an end of the lead screw 34. The lead screw 34, the plunger 36 and the reservoir 22 are adapted (e.g., provided with o-rings) such that a fluid-tight seal is formed between the plunger 36 and the lead screw 34 and a fluid-tight seal is formed between the plunger 36 and the side wall 30 of the reservoir 22, so that movement of the plunger 36 towards the outlet 32 of the reservoir 22 forces fluid through the outlet 32 to the transcutaneous access tool 24.

Figure 7A:
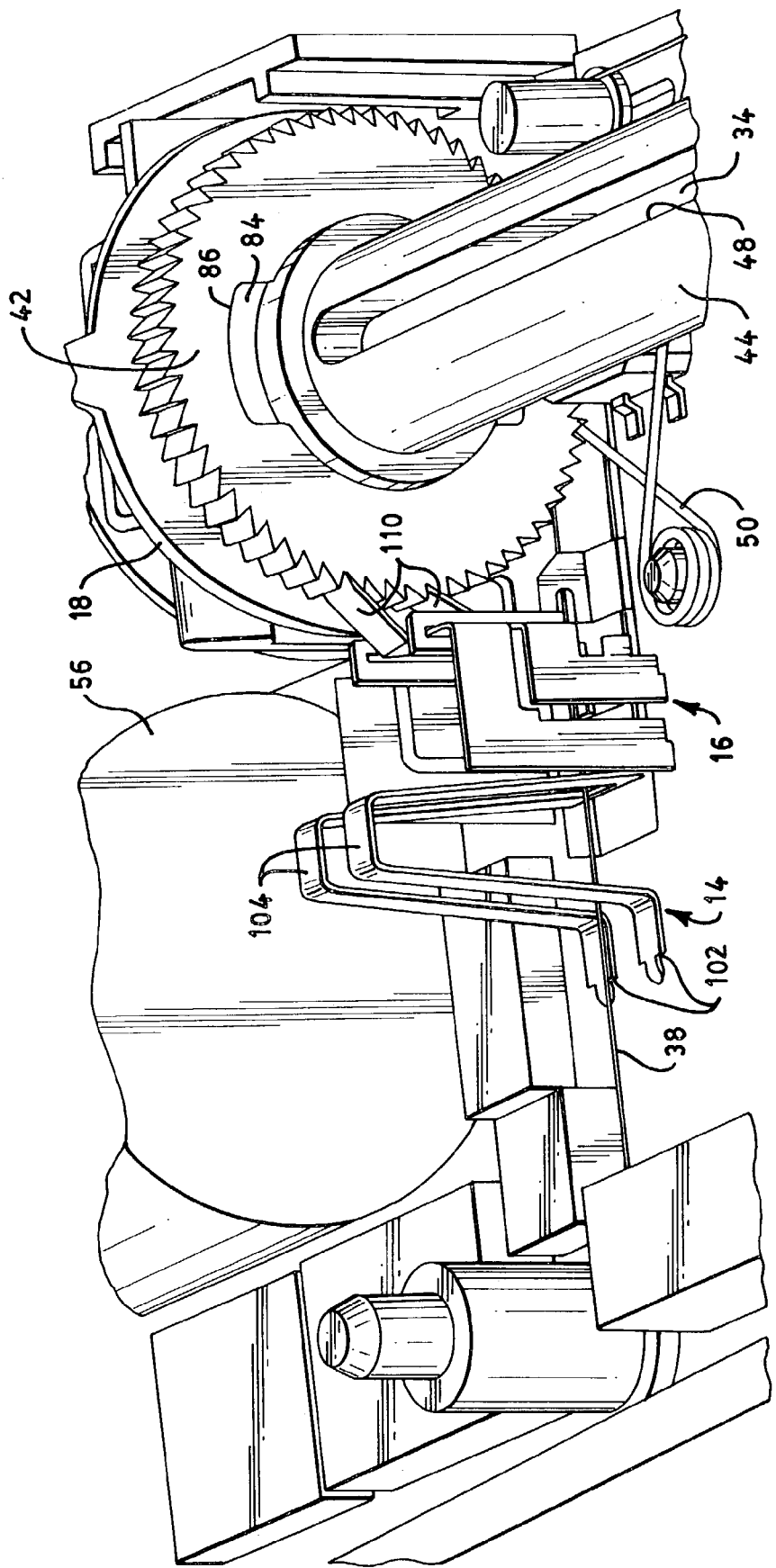
FIG. 7a is a further enlarged top perspective view of a portion of the fluid delivery device of FIG. 1, shown with the top housing portion removed to reveal interior portions of the fluid delivery device, including the lead screw assembly and exemplary embodiments of a set of pawls and a ratchet member constructed in accordance with the present invention.

As shown in FIG. 7a, the device 10 includes an actuator in the form of an elongated shape memory element 38 operatively connected to a processor 40 of the fluid delivery device such that electrical charges can be applied to the shape memory element based on commands from the processor. The shape memory element 38 has a changeable length decreasing from an uncharged length to a charged length when at least one charge is applied to the shape memory element 38, and is operatively connected to the lead screw assembly 12 through the ratchet member 14 such that the changeable length of the shape memory element 38 causes longitudinal movement of the lead screw 34 so that the plunger 36 moves along the side wall 30 of the reservoir 22.

In the exemplary embodiment shown in FIG. 3, a rotatable gear 42 is coaxially fixed to an exterior surface of a slotted tube 44 of the lead screw assembly 12 such that rotation of the gear 42 causes rotation of the slotted tube 44 about a common longitudinal axis "A". The lead screw 34 is coaxially positioned within the slotted tube 44 and includes a radially extending pin 46 slidingly received in longitudinal slots 48 of the slotted tube 44 such that rotation of the slotted tube 44 causes rotation of the lead screw 34. The lead screw 34 is also threadedly engaged with the fixed nut assembly 18, which is non-rotating with respect to the lead screw 34 and is linearly fixed in position with respect to the reservoir 22. Rotation of the gear 42 causes linear movement of the lead screw 34 through the fixed nut assembly 18 and linear movement of the plunger 36 towards the outlet 32 of the reservoir 22.

The ratchet member 14 engages radially extending teeth of the gear 42, and the ratchet member 14 and the gear 42 are adapted such that linear movement of the ratchet member 14 in a first direction adjacent the gear 42 causes rotation of the gear 42, while linear movement of the ratchet member 14 in a second direction adjacent the gear 42 causes no rotation of the gear 42. The elongated shape memory element 38, shown in FIG. 7a, is connected to the ratchet member 14 such that the changeable length of the shape memory element 38 decreasing from an uncharged length to a charged length causes linear movement of the ratchet member 14 in one of the first and the second directions. A spring 50, as shown best in FIG. 7a, is connected to the ratchet member 14 for causing linear movement of the ratchet member 14 in the other of the first and the second directions. In the exemplary embodiment shown, the spring comprises a hinge spring 50.

The processor 40 (hereinafter referred to as the "local" processor) is electrically connected to the shape memory element 38 and is programmed to apply charges to the shape memory element in order to cause a flow of fluid to the transcutaneous access tool 24, based on flow instructions from a separate, remote control device 1000, an example of which is shown in FIG. 1. A wireless receiver 52 is connected to the local processor 40 for receiving flow instructions from the remote control device 1000 and delivering the flow instructions to the local processor 40. The device 10 also includes a housing 54 containing the lead screw assembly 12, the ratchet member 14, the set of pawls 16, the fixed nut assembly 18, the sensor assembly 20, the flow path assembly 26, the transcutaneous access tool 24, the reservoir 22, the local processor 40, and the wireless receiver 52.

As shown best in FIGS. 2a and 2b, the housing 54 of the fluid delivery device 10 is free of user input components for providing flow instructions to the local processor 40, such as electromechanical switches or buttons on an outer surface of the housing 54, or interfaces otherwise accessible to a user to adjust the programmed flow rate through the local processor 40. The lack of user input components allows the size, complexity and costs of the device 10 to be substantially reduced so that the device 10 lends itself to being small and disposable in nature. Examples of such devices are disclosed in U.S. patent application Ser. No. 09/943,992, filed on Aug. 31, 2001, and entitled DEVICES, SYSTEMS AND METHODS FOR PATIENT INFUSION, which is assigned to the assignee of the present application and has previously been incorporated herein by reference.

In order to program, adjust the programming of, or otherwise communicate user inputs to the local processor 40, the fluid delivery device 10 includes the wireless communication element 52, as shown in FIG. 3, for receiving the user inputs from the separate, remote control device 1000 of FIG. 1. Signals can be sent via a communication element (not shown) of the remote control device 1000, which can include or be connected to an antenna 1300, shown in FIG. 1 as being external to the device 1000.

The remote control device 1000 has user input components, including an array of electromechanical switches, such as the membrane keypad 1200 shown. The remote control device 1000 also includes user output components, including a visual display, such as a liquid crystal display (LCD) 1100. Alternatively, the control device 1000 can be provided with a touch screen for both user input and output. Although not shown in FIG. 1, the remote control device 1000 has its own processor (hereinafter referred to as the "remote" processor) connected to the membrane keypad 1200 and the LCD 1100. The remote processor receives the user inputs from the membrane keypad 1200 and provides "flow" instructions for transmission to the fluid delivery device 10, and provides information to the LCD 1100. Since the remote control device 1000 also includes a visual display 1100, the fluid delivery device 10 can be void of an information screen, further reducing the size, complexity and costs of the device 10.

The communication element 52 of the device 10 preferably receives electronic communication from the remote control device 1000 using radio frequency or other wireless communication standards and protocols. In a preferred embodiment, the communication element 52 is a two-way communication element, including a receiver and a transmitter, for allowing the fluid delivery device 10 to send information back to the remote control device 1000. In such an embodiment, the remote control device 1000 also includes an integral communication element comprising a receiver and a transmitter, for allowing the remote control device 1000 to receive the information sent by the fluid delivery device 10.

The local processor 40 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 40 also includes programming, electronic circuitry and memory to properly activate the shape memory element 38 at the needed time intervals.

In the exemplary embodiment of FIG. 3, the device 10 also includes a power supply, such as a battery or capacitor 56, for supplying power to the local processor 40. The power supply 56 is preferably integrated into the fluid delivery device 10, but can be provided as replaceable, e.g., a replaceable battery. The device 10 can also include sensors or transducers such as a flow condition sensor assembly 58, for transmitting information to the local processor 40 to indicate how and when to activate the shape memory element 38, or to indicate other parameters determining fluid flow, as well as conditions such as the reservoir 22 being empty or leaking, or the dispensing of too much or too little fluid from the reservoir 22, etc.

As shown in FIG. 2b, the device 10 can also be provided with an adhesive layer 60 on the outer surface of the housing 54 for securing the device 10 directly to the skin of a patient, as illustrated in FIG. 1. The adhesive layer 60 is provided on an external "bottom" surface of the housing 54. The adhesive layer 60 is also preferably provided in a continuous ring encircling an external exit port 62 of the housing 54 in order to provide a protective seal around the penetrated patient's skin to prevent the penetrated skin from becoming contaminated when a cannula 64 of the transcutaneous access tool 24 extends through the skin. It is preferable that the fill port 28 extend through the bottom surface of the housing 54 and be surrounded by the adhesive layer 60 to discourage and prevent filling and re-filling of the fluid delivery device 10 when the device is attached to a patient's skin. The housing 54 can be made from flexible material, or can be provided with flexible hinged sections that allow the fluid delivery device 10 to flex during patient movement to prevent detachment and aid in patient comfort.

Figure 4:
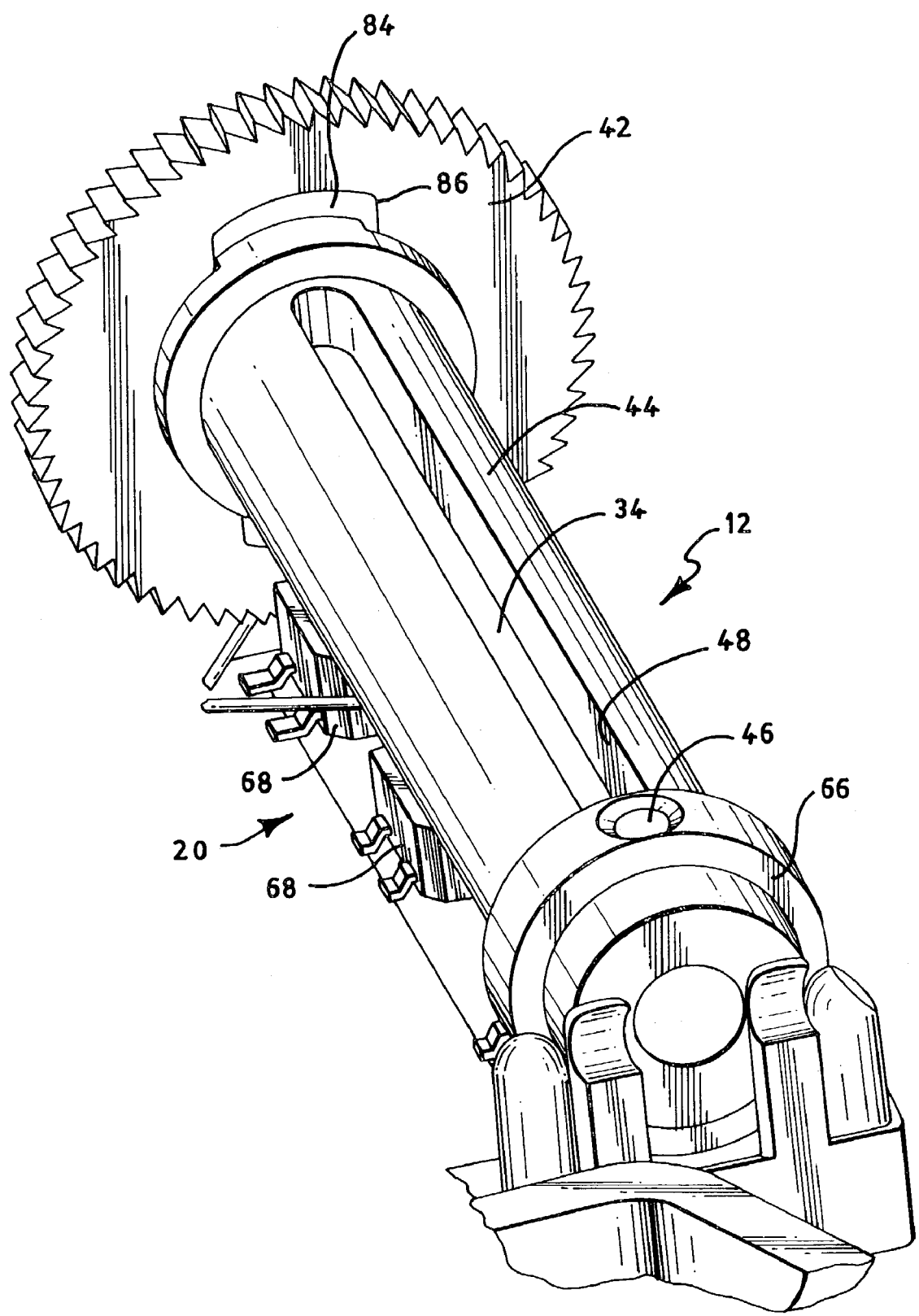
FIG. 4 is a further enlarged perspective view of the lead screw assembly of the fluid delivery device of FIG. 1.

The sensor assembly 20 monitoring longitudinal movement of the lead screw 34 includes a reference element 66 secured to the pin 46 of the lead screw 34, at least one light emitter directed laterally at the tube 44 for directing a beam of light at the tube 44, and at least one light detector directed laterally at the tube 44 for receiving the beam of light reflected away from the tube 44. In the exemplary embodiment of FIGS. 3 and 4, the light emitter and the light detector are provided as part of a single component, i.e., a light emitter/detector 68. In addition, one of the tube 44 and the reference element 66 has a light reflective outer surface, so that the detector 68 provides a signal upon movement of the reference element past the detector. In the exemplary embodiment shown in FIGS. 3 through 5, the reference element 66 has a light reflective outer surface. In addition, the reference element 66 is annular and coaxially received for sliding movement along an outer surface of the tube 44. Moreover, as shown in FIGS. 3 and 4, the sensor assembly 20 includes three of the emitter/detectors 68.

This configuration provides absolute position information regarding the lead screw 34 and thus the plunger position. When a signal is received indicating that the reference element 66 has been detected by detector 68, the information is interpreted as to a specific amount of fluid residing in the reservoir. Multiple detectors, such as detector 68, can be utilized to provide multiple levels of reservoir volume (absolute position of lead screw). For example, one detector can be positioned at a relatively low volume to indicate to the user the pump is near empty. An opposite configuration can be employed, wherein a single detector (relatively more expensive than the reference element) is secured for movement to the pin 46 and one or more reference elements 66 are directed laterally at the tube. In a exemplary embodiment, the detector is annular and coaxially received for sliding movement along the outer surface of the tube 44. This configuration requires (moving) wires connected to the detector.

The fixed nut assembly 18 is configured to be disengaged from the lead screw 34 prior to use of the device 10 to allow the lead screw 34 and the plunger 36 to be linearly moved away from an inlet 33 of the reservoir 22 during filling of the reservoir 22 through the fill port 18. Referring also to FIGS. 5, 6a, 6b and 6c, the exemplary embodiment of the fixed nut assembly 18 includes at least two laterally movable threaded inserts 70 including threaded surfaces for threadedly receiving the lead screw 34 upon being biased laterally inwardly against the lead screw 34, a spring 72 biasing the threaded inserts 70 laterally inwardly against the lead screw 34, and at least one spacer cam 74 movable between a first position preventing the threaded inserts 70 from being biased laterally inwardly against the lead screw 34 and a second position allowing the threaded inserts 70 to be biased laterally inwardly against the lead screw 34.

Figure 6A:
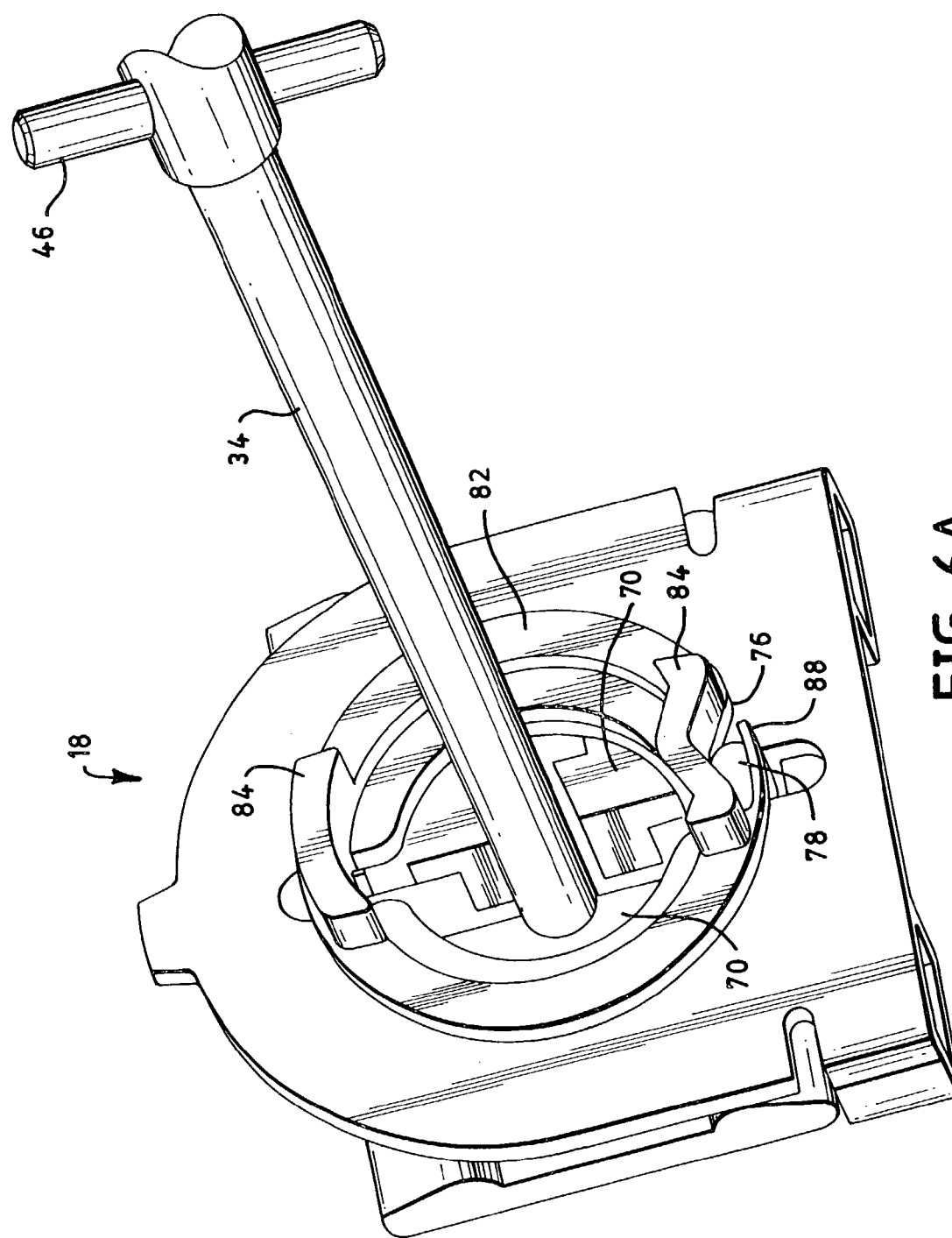
FIG. 6a is a further perspective view of a portion of the lead screw assembly of the fluid delivery device of FIG. 1, including an exemplary embodiment of a fixed nut assembly constructed in accordance with the present invention.
Figure 6B:
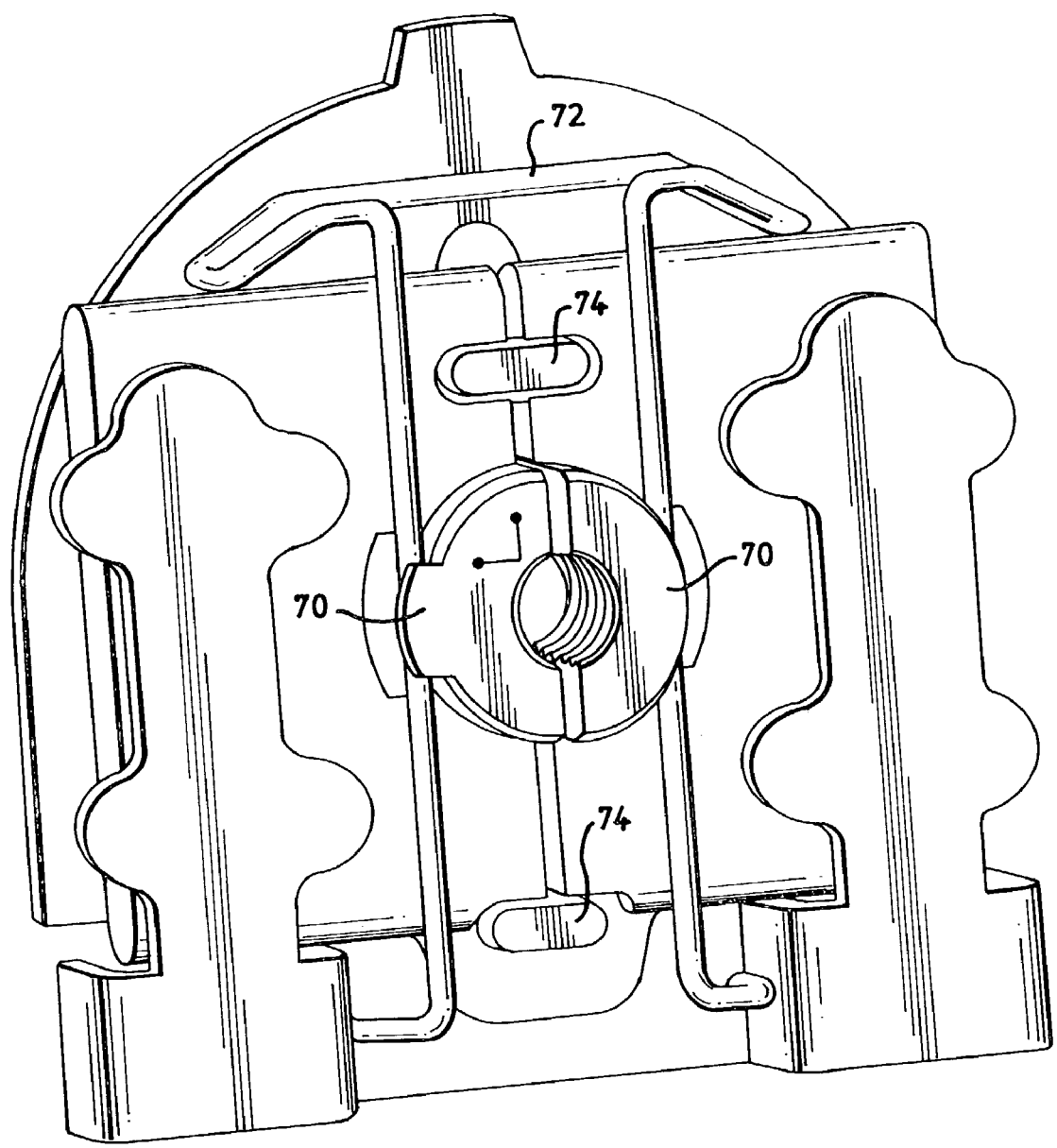
FIG. 6b is another perspective view of the fixed nut assembly of the fluid delivery device of FIG. 1.
Figure 6C:
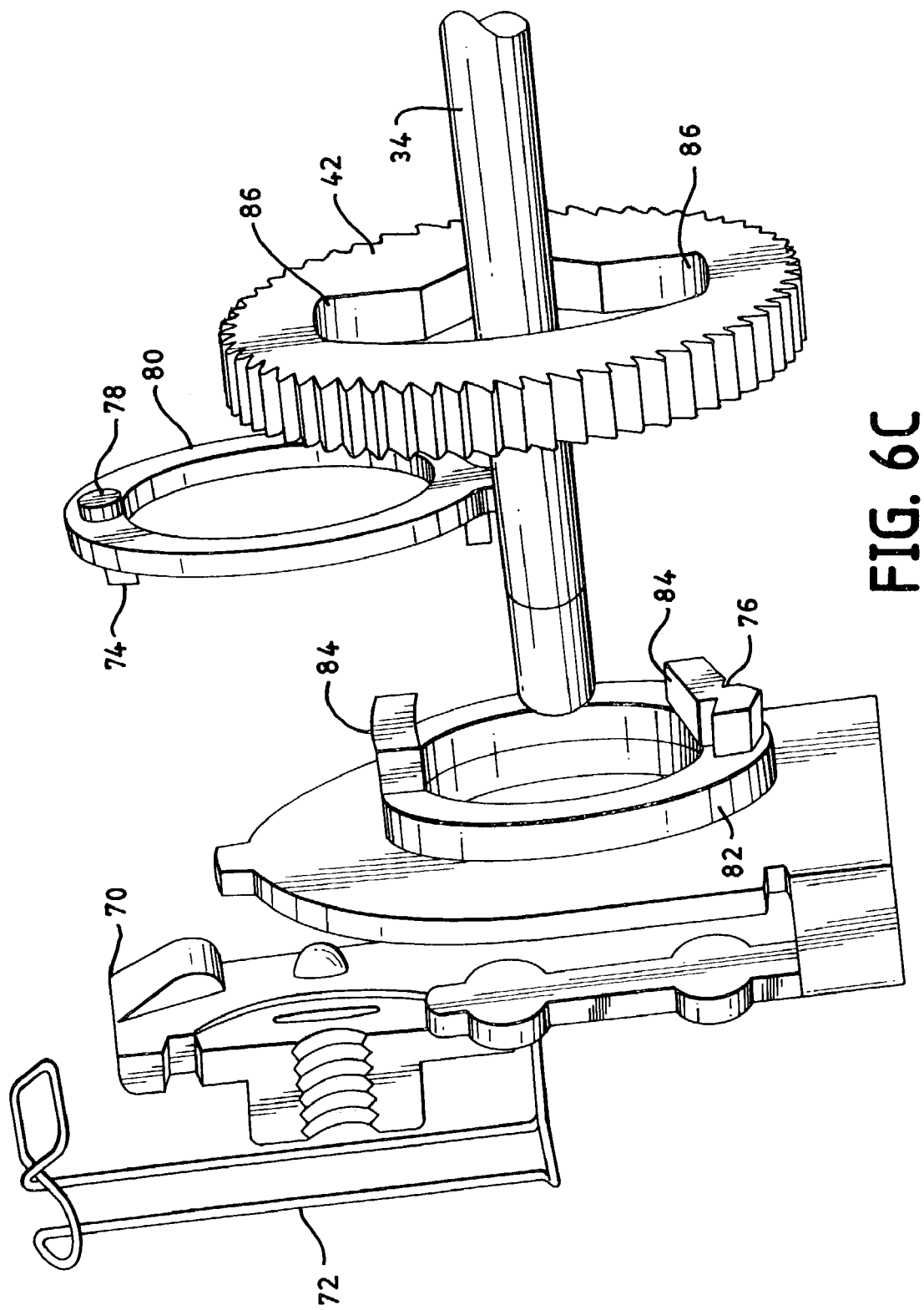
FIG. 6c is an exploded, perspective view of portions of the fixed nut assembly of the fluid delivery device of FIG. 1.

In the exemplary embodiment of FIGS. 6a, 6b and 6c, the spacer cams 74 are laterally movable with respect to the lead screw 34, and are adapted so that, in the first position, the spacer cams 74 are positioned between the threaded inserts 70. Preferably, the spacer cams 74 are operatively connected to the gear 42 such that rotation of the gear 42 causes movement of the spacer cams 74 to the second position. In this manner, the initial rotation of the gear 42, when the device 10 is first used (i.e., powered-up or started), can be used to engage the nut assembly 18 and the lead screw 34, such that further rotation of the gear 42 causes linear movement of the lead screw 34.

The nut assembly 18 also includes a gear cam 76 operatively connected with the gear 42 for rotation with the gear 42 about the lead screw 34, and a spacer follower 78 laterally moveable with respect to the lead screw 34. The spacer follower 78 is connected to the spacer cams 74 such that lateral movement of the spacer follower 78 in a first direction with respect to the lead screw 34 causes movement of the spacer cams 74 to the second position. The spacer follower 78 is received against the gear cam 76 and the gear cam 76 and the spacer follower 78 are shaped such that rotation of the gear cam 76 about the lead screw 34 (i.e., rotation of the gear 42) causes lateral movement of the spacer follower 78 in the first direction with respect to the lead screw 34.

In the exemplary embodiment shown in FIGS. 6a, 6b and 6c, the spacer follower 78 and the spacer cams 74 are connected through a spacer ring 80 coaxially positioned with respect to the lead screw 34. In addition, the gear cam 76 is provided as part of a gear ring 82 coaxially positioned with respect to the lead screw 34 and including at least one spline 84 extending into a keyway 86 of the gear 42. The gear cam 76 is formed in a radially outwardly facing surface of one of the splines 84.

Figure 5:
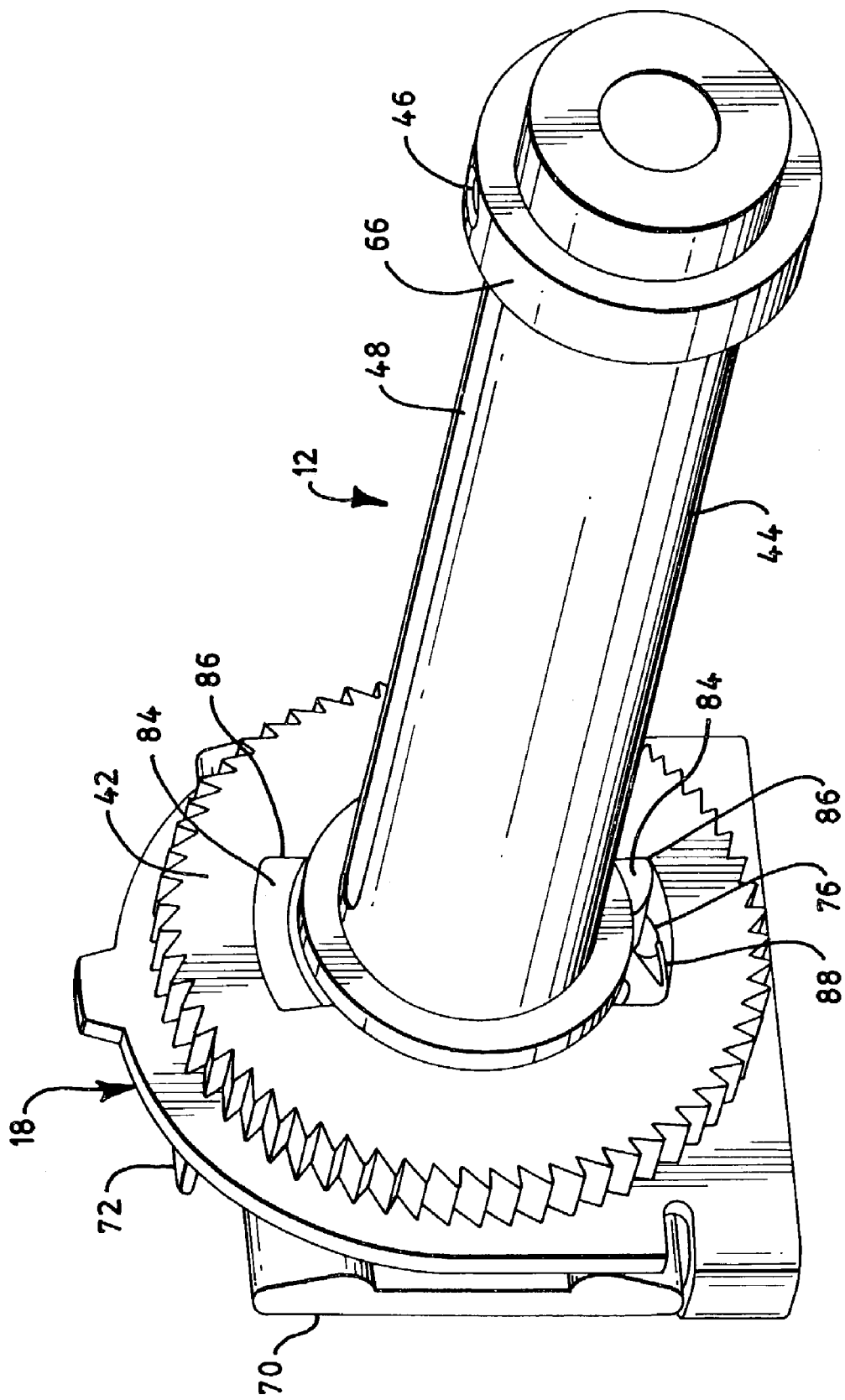
FIG. 5 is another perspective view of the lead screw assembly of the fluid delivery device of FIG. 1.

As shown best in FIGS. 5 and 6a, the gear ring 82 also includes a latch 88 allowing the spacer follower 78 to exit the gear cam 76 and preventing the spacer follower 78 from re-entering the gear cam 76. In this manner, after the gear 42 is initially turned, the nut assembly 18 engages the lead screw 34 and remains engaged with the lead screw 34 even upon one or more full rotations of the gear 42.

Figure 20:
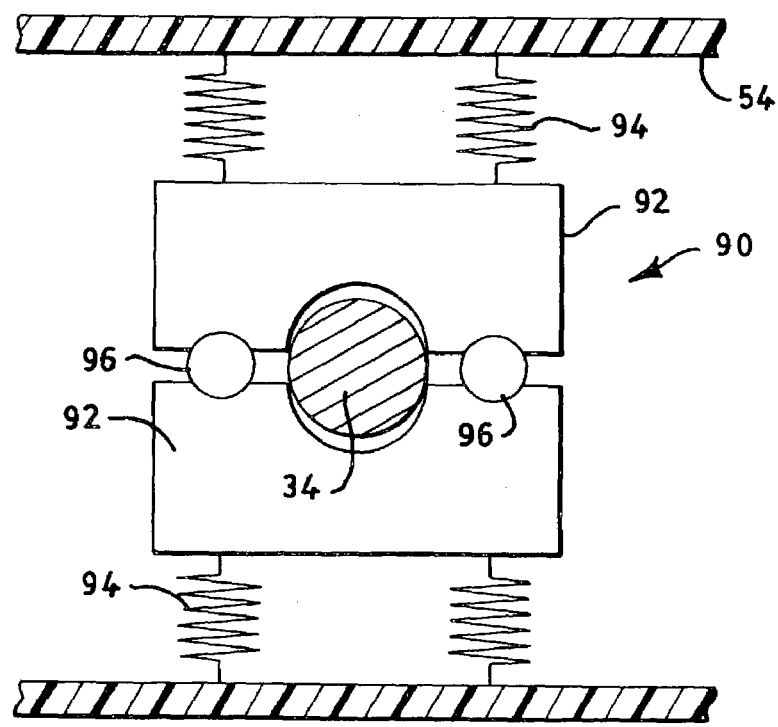
FIG. 20 is a schematic illustration of another exemplary embodiment of a fixed nut assembly and a lead screw constructed in accordance with the present invention, for use with a fluid delivery device such as the fluid delivery device of FIG. 3.

Another exemplary embodiment of a nut assembly 90 constructed in accordance with the present invention is shown in FIG. 20. The nut assembly 90 includes at least two laterally movable threaded inserts 92 having threaded surfaces for threadedly receiving the lead screw 34 upon being biased laterally inwardly against the lead screw, springs 94 biasing the threaded inserts 92 laterally inwardly against the lead screw 34, and spacer cams 96. The spacer cams 96 are movable in a longitudinal direction with respect to the lead screw 34 between a first position preventing the threaded inserts 92 from being biased laterally inwardly against the lead screw, as shown in FIG. 20, and a second position allowing the threaded inserts 92 to be biased laterally inwardly against the lead screw. It is intended that the spacer cams 96 can be adapted to be manually moved to the second position by a user once the user has filled the reservoir. In one possible embodiment, the spacer cams 96 may have an extension portion that extends out of the housing of the fluid delivery device for manual movement of the spacer cams 96 by a user.

It should be understood, however, that other mechanisms can be employed which have one or more threaded parts which are not initially engaged with, or can be disengaged from, the lead screw 34 and that allow linear motion of the lead screw without requiring rotation of the lead screw, and that later can be engaged with the lead screw 34 to allow linear motion of the lead screw only upon rotation of the lead screw. Engagement and disengagement of the lead screw 34 can be accomplished as described above, or by other means such as via a linear actuator (e.g. an shape memory element "pulls" the threaded member(s) away from the lead screw to allow freedom of movement of the lead screw during filling of the reservoir).

Figure 7B:
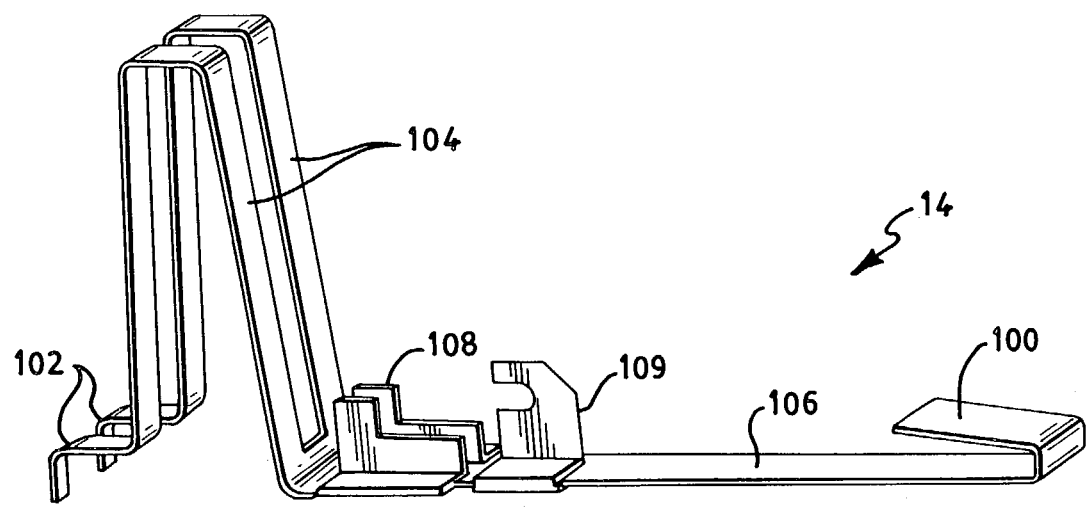
FIG. 7b is a further enlarged perspective view of the ratchet member of the fluid delivery device of FIG. 1.

Referring now to FIGS. 3, 7a and 7b, the ratchet member 14 includes a ratchet 100 engaging teeth of the gear 42, at least one anchor 102 fixed in position with respect to the gear 42, and at least one spring 104 biasing the ratchet 100 in the second direction and away from the anchor 102. The springs 104 comprise bent portions of flat sheet material. The ratchet 100 is connected to the springs 104 through a flat extension portion 106, which also is biased away from the anchors 102 by the springs 104. The flat extension portion 106 also includes bosses 108, 109 for connection to the shape memory element 38 and the ratchet spring 50. The ratchet member 14 is preferably formed from a single piece of sheet metal, which is cut, bent and folded to form the anchors 102, the springs 104, flat extension portion 106, the ratchet 100 and the bosses 108, 109. In the exemplary embodiment shown, the shape memory element 38 is arranged such that the changeable length of the shape memory element decreasing from an uncharged length to a charged length causes movement of the ratchet 100 in the first direction. The hinge spring 50 is arranged to bias the ratchet 100 in the second direction.

Figure 7C:
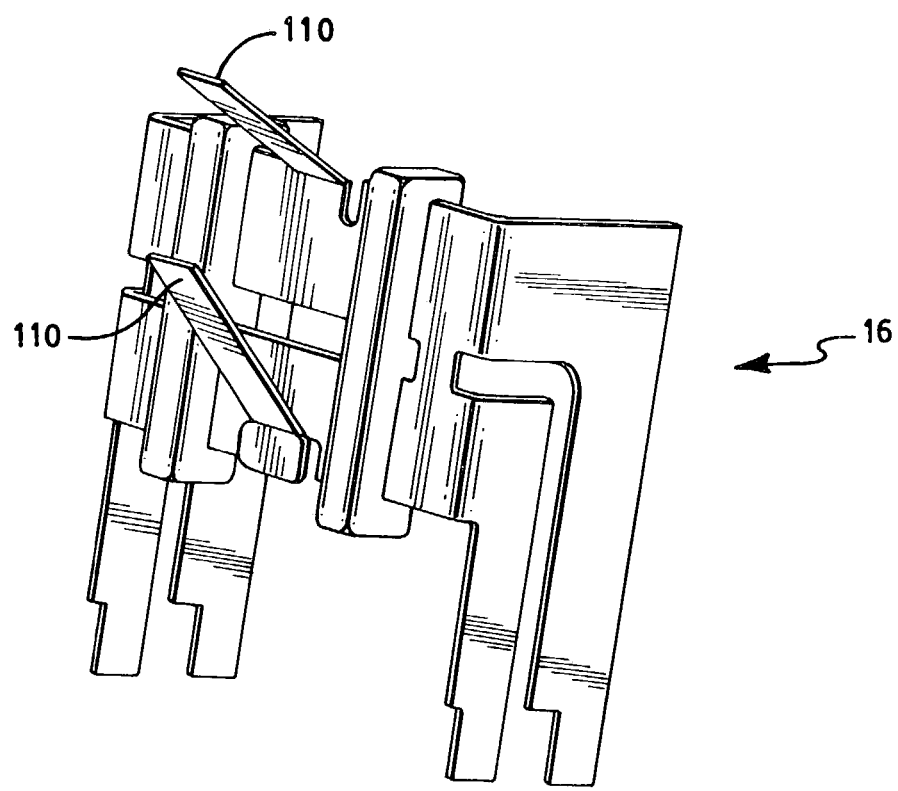
FIG. 7c is a further enlarged, opposite perspective view of the set of pawls of the fluid delivery device of FIG. 1.

Referring back to FIGS. 7a and 7c, the set of pawls 16 includes at least two pawls 110 engaging teeth of the gear 42 and allowing rotation of the gear 42 in a single direction. The pawls 110 allow rotation of the gear 42, and thus the tube 44 and the lead screw 34, in a single direction, which in the exemplary embodiment of FIG. 7a is shown as being clockwise. Among other features and benefits, the deployment of at least two pawls 110 provides redundancy in case one of the pawls 110 snaps or otherwise fails during operation of the device. According to one exemplary embodiment, the pawls 110 are adapted and arranged such that the pawls 110 allow rotation of the gear equal to less than a tooth pitch of the gear. For example in one embodiment, the pawls 110 are provided with the same length, but are arranged to be out of phase by a single tooth pitch in order to allow rotation of the gear equal to less than a tooth pitch of the gear. According to another exemplary embodiment, the pawls 110 are arranged to be in phase but are provided with different lengths in order to allow rotation of the gear equal to less than a tooth pitch of the gear.

Figure 8:
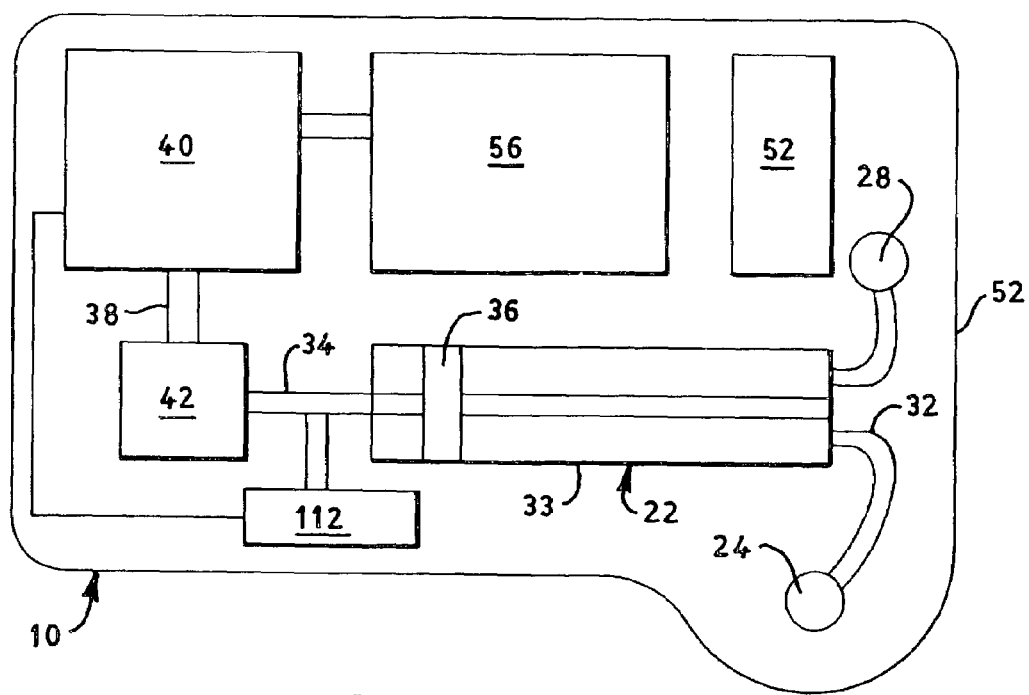
FIG. 8 is a schematic illustration of components of an exemplary embodiment of a fluid delivery device constructed in accordance with the present invention and including a lead screw and a sensor for providing signals indicative of longitudinal movement of the lead screw.

Referring now to FIG. 8, an embodiment of the present invention is provided with a sensor 112 detecting linear movement of the lead screw 34. The sensor 112 can be provided in many forms, such as the optical emitter/detectors 68 of FIGS. 3 and 4, for providing a signal indicative of longitudinal movement of the lead screw 34. Longitudinal movement of the lead screw 34 towards the outlet 32 of the reservoir 22, of course, indicates a corresponding movement of the plunger 36 and the dispensing of fluid from the reservoir to the transcutaneous access tool 24.

The processor 40 is connected to the sensor 112 and programmed to apply a charge to the shape memory element 38 (as generally based upon the desire fluid flow as programmed by a user through the remote control device), and remove the charge upon receiving a signal from the sensor 112 indicative of a desired amount, preferably a minimum amount, of linear movement of the lead screw 34. In this manner, power is applied to the shape memory element 38 only for as long as needed to cause movement of the lead screw 34 as desired. In an alternative, preferred embodiment, a construction is employed, some of which are described herebelow, which detects a desired amount of rotation of the lead screw prior to removing the charge from the shape memory element 38. The addition of the sensor 112 and the programming of the processor 40 results in a reduction in power usage by the fluid delivery device 10, since power is only applied to the shape memory element 38 for a period necessary to advance the plunger 36 by a desired amount (i.e. the efficiency of the drive system is improved by minimizing power loss to the shape memory component).

Figure 9:
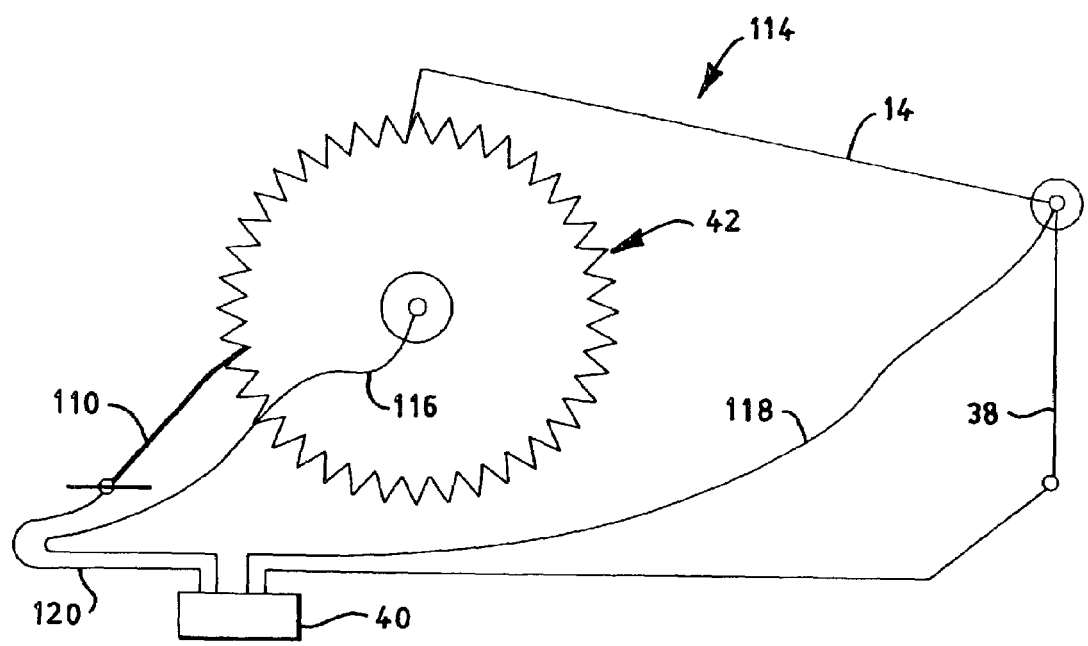
FIG. 9 is a schematic illustration of an exemplary embodiment of sensor assembly constructed in accordance with the present invention for providing an indication of rotation of a gear of a fluid delivery device, such as the fluid delivery device of FIG. 3.

FIG. 9 shows an embodiment of a sensor assembly 114 constructed in accordance with the present invention for providing signals indicating rotation of the gear 42. Rotation of the gear 42, in turn, provides an indication of longitudinal movement of the lead screw 34. The sensor assembly 114 includes a first electrical lead 116 connected to the gear 42, a second electrical lead 118 connected to the ratchet 100, and a third electrical lead 120 connected to the pawl 110. In the embodiment of FIG. 9, the gear 42, the ratchet 100, and the pawl 110 are made from electrically conductive material. The processor 40 is connected to the first, the second and the third electrical leads 116, 118, 120 and programmed to determine whether the gear 42 has been rotated based at least in part on electrical discontinuities between the ratchet 100, the gear 42, and the pawl 110 (i.e., opening and closing of the circuit formed between the ratchet, the gear, and the pawl as the gear rotates).

Figure 10:
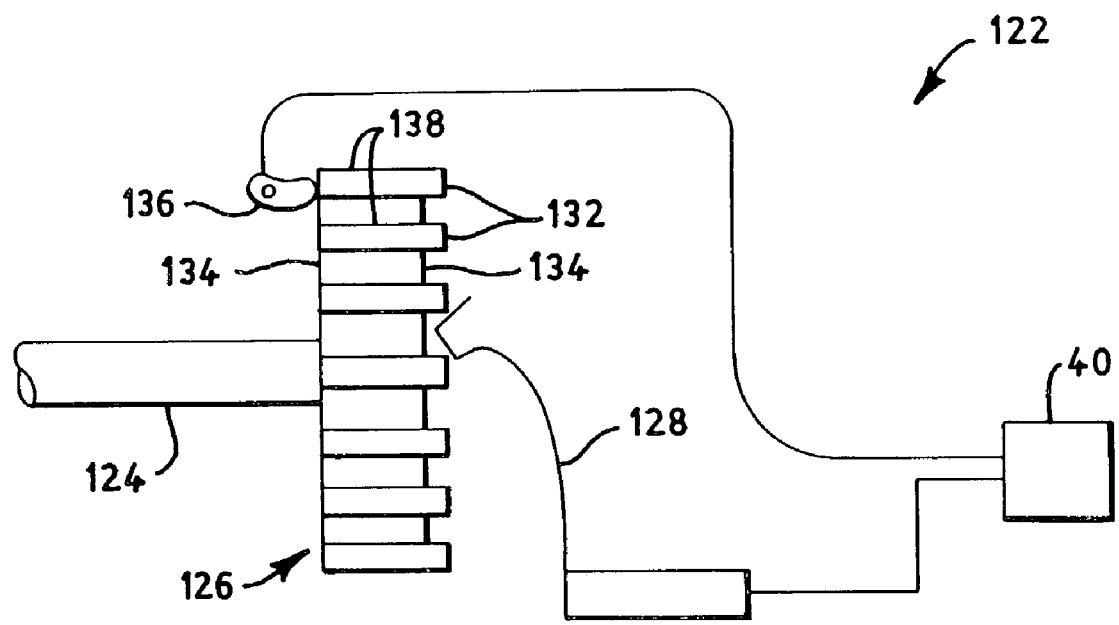
FIG. 10 is a side elevation view of another exemplary embodiment of sensor assembly constructed in accordance with the present invention for providing an indication of rotation of a gear of a fluid delivery device, such as the fluid delivery device of FIG. 3.
Figure 11:
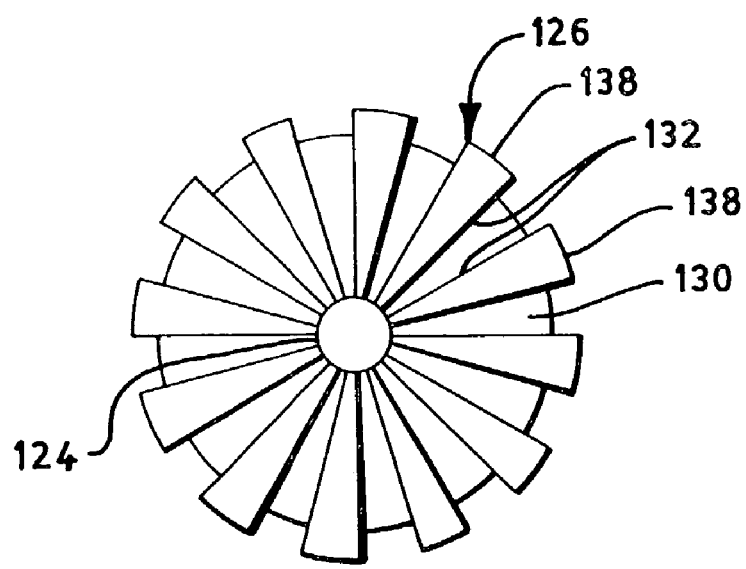
FIG. 11 is an end elevation view of the gear of FIG. 10.

FIGS. 10 and 11 show another exemplary embodiment of a sensor assembly 122 constructed in accordance with the present invention for use as part of a fluid delivery device, such as the fluid delivery device 10 of FIG. 3. The sensor assembly 122 can be used to provide an indirect indication of longitudinal movement of a lead screw 124, and includes a gear 126 and an electrically conductive brush 128 biased against a face 130 of the gear. The gear 126 is intended to be operatively connected to the lead screw 124, similar to the gear 42 and the lead screw 34 of FIG. 3 for example. Rotation of the gear 126, accordingly, causes longitudinal movement of the lead screw 124.

As shown, the face 130 of the gear 126 includes radially spaced bumps 132 thereon. One of the face 130 and the bumps 132 are electrically conductive. In the exemplary embodiment shown, an opposite, second face 134 of the gear 126 is made from, or covered by electrically conductive material, and a second electrically conductive brush 136 is biased against the second face 134 of the gear. Both brushes 128, 136 are then connected to a processor 40 which is programmed to determine whether the gear 126 has rotated based at least in part on electrical discontinuities between the brushes 128, 136 and the gear (i.e., opening and closing of the circuit formed between the brush 128 and the bumps 132 of the gear 126 as the gear rotates). In the exemplary embodiment shown in FIGS. 10 and 11, the radially spaced bumps 132 are made of conductive material and correspond to outer circumferential teeth 138 of the gear 126.

Figure 12:
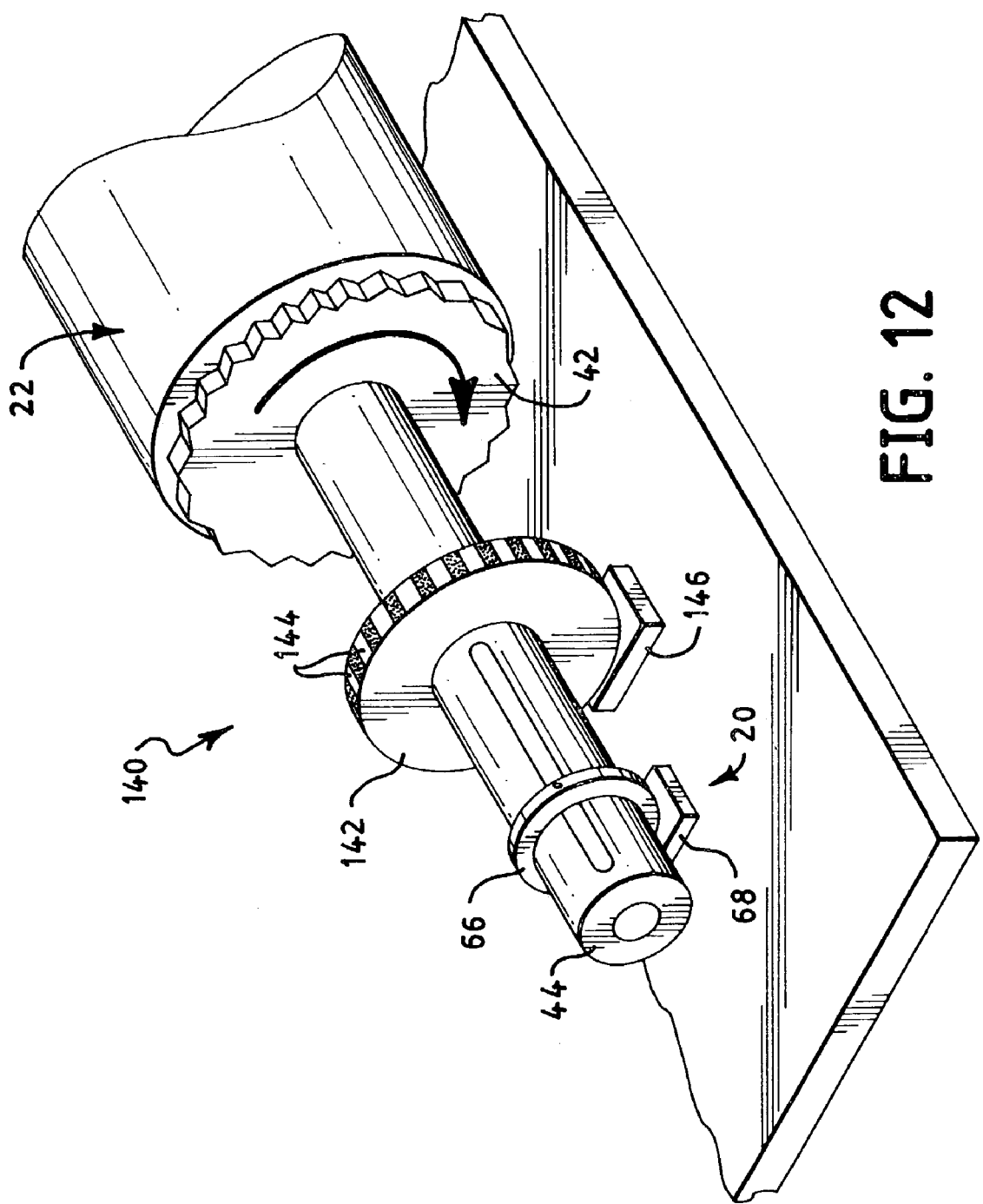
FIG. 12 is a perspective view of an exemplary embodiment of sensor assembly constructed in accordance with the present invention for providing an indication of rotation of a lead screw assembly of a fluid delivery device, such as the fluid delivery device of FIG. 3.
Figure 13:
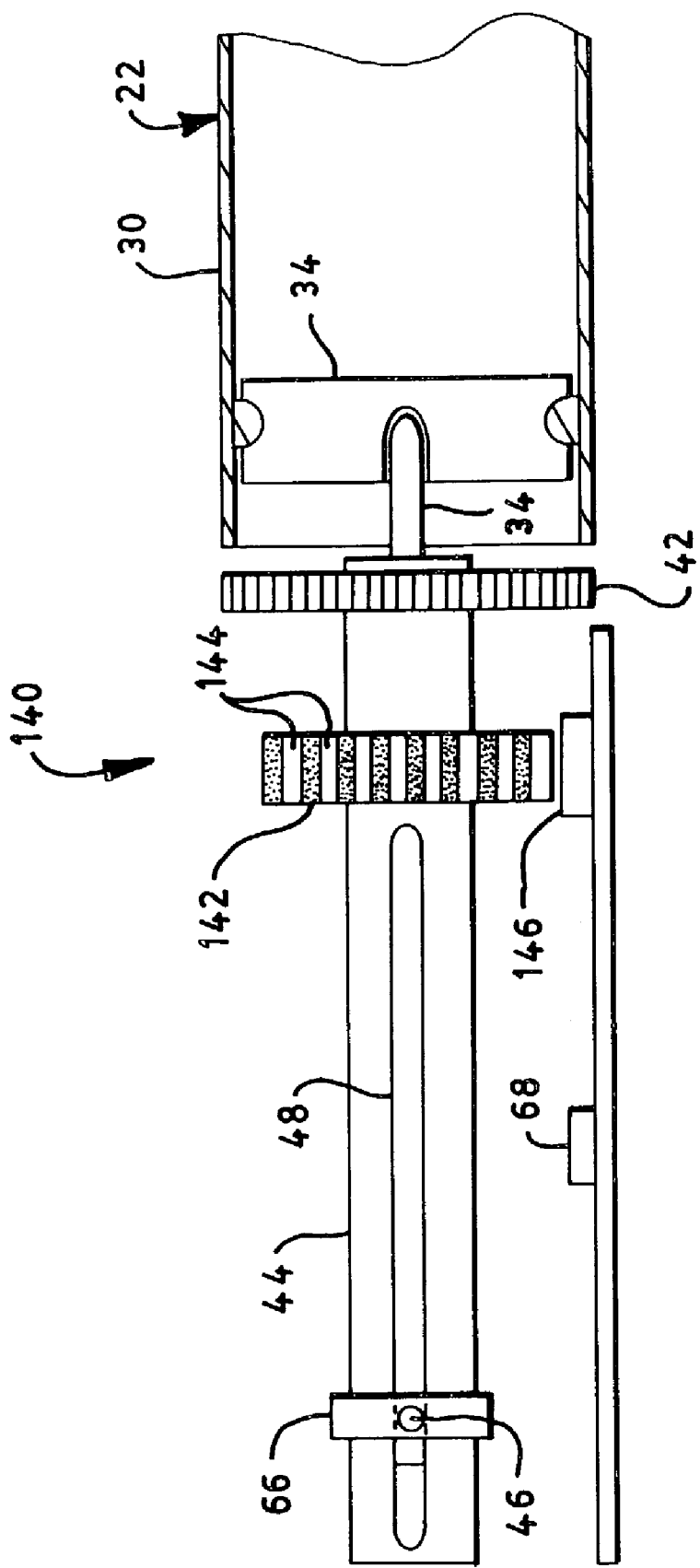
FIG. 13 is a side elevation view of the sensor assembly and the lead screw assembly of FIG. 12.

FIGS. 12 and 13 show a further exemplary embodiment of sensor assembly 140 constructed in accordance with the present invention for use as part of a fluid delivery device, such as the fluid delivery device 10 of FIG. 3. The sensor assembly 140 can be used to provide an indirect indication of longitudinal movement of the lead screw 34, and includes an encoder disk 142 coaxially secured to the tube 44 and including radially spaced light reflective indicia 144 thereon. A light emitter is directed at the encoder disk, and a light detector directed at the encoder disk. In the exemplary embodiment shown, the light emitter and the light detector are combined in a single light emitter/detector 146. The light emitter/detector 146 is connected to the processor (not shown) of the fluid delivery device, which is in-turn programmed to determine the amount of rotation of the tube 44, and thus the connected gear 42 and the lead screw 34. In the exemplary embodiment of FIGS. 12 and 13, the radially spaced light reflective indicia 144 is located on an outer circumferential surface of the encoder disk 142.

Figure 14:
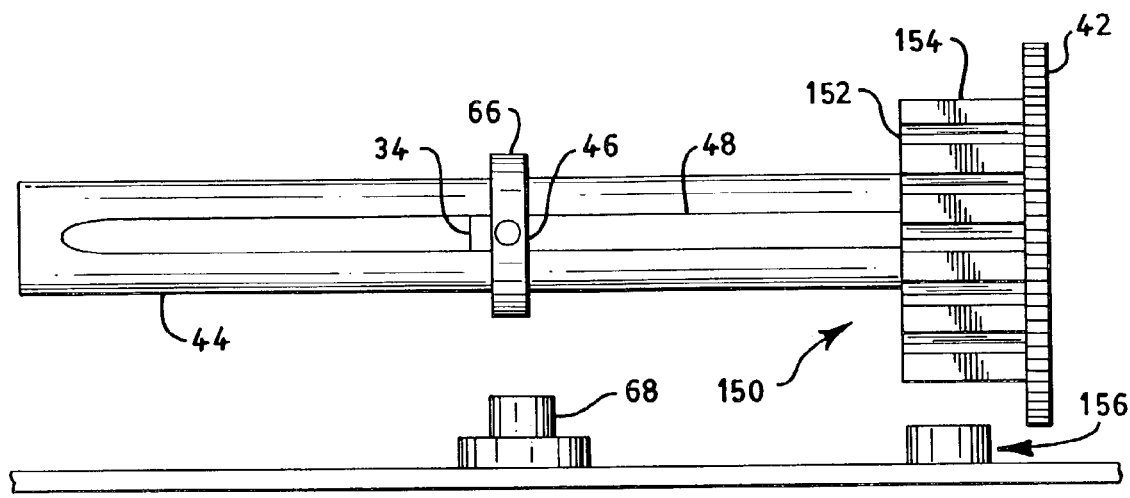
FIG. 14 is a side elevation view of another exemplary embodiment of sensor assembly constructed in accordance with the present invention for providing an indication of rotation of a lead screw assembly of a fluid delivery device, such as the fluid delivery device of FIG. 3.
Figure 15:
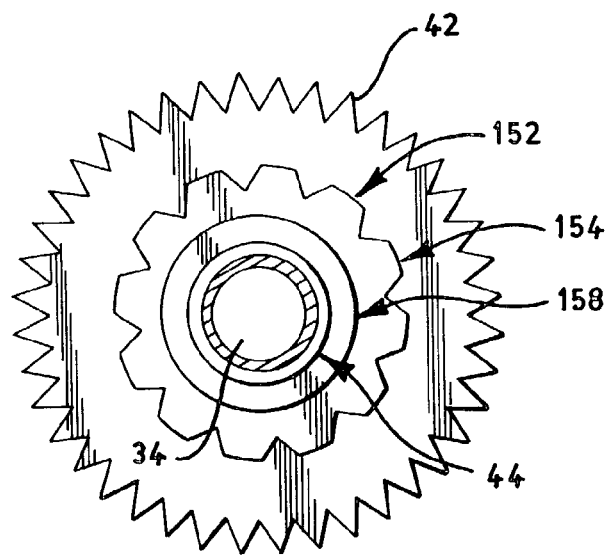
FIG. 15 is an end elevation view of an encoder disk of the sensor assembly of FIG. 14.

FIGS. 14 and 15 show still another exemplary embodiment of sensor assembly 150 including an encoder disk 152 coaxially secured to the tube 44 and including radially spaced light reflective indicia 154 thereon. A light emitter/detector 156 is directed at the encoder disk 152, and is connected to the processor (not shown) of the fluid delivery device. The processor is in-turn programmed to determine the amount of rotation of the tube 44, and thus the connected gear 42 and the lead screw 34. In the exemplary embodiment of FIGS. 14 and 15, the radially spaced light reflective indicia 154 is located on an outer circumferential surface of the encoder disk 152. In addition, the encoder disk 152 is secured to the gear 42 and includes a recess 158 on a face thereof for receiving the annular reference element 66 (which is secured to the lead screw 34) in a nested manner upon the lead screw 34 being fully moved into the reservoir.

Figure 16:
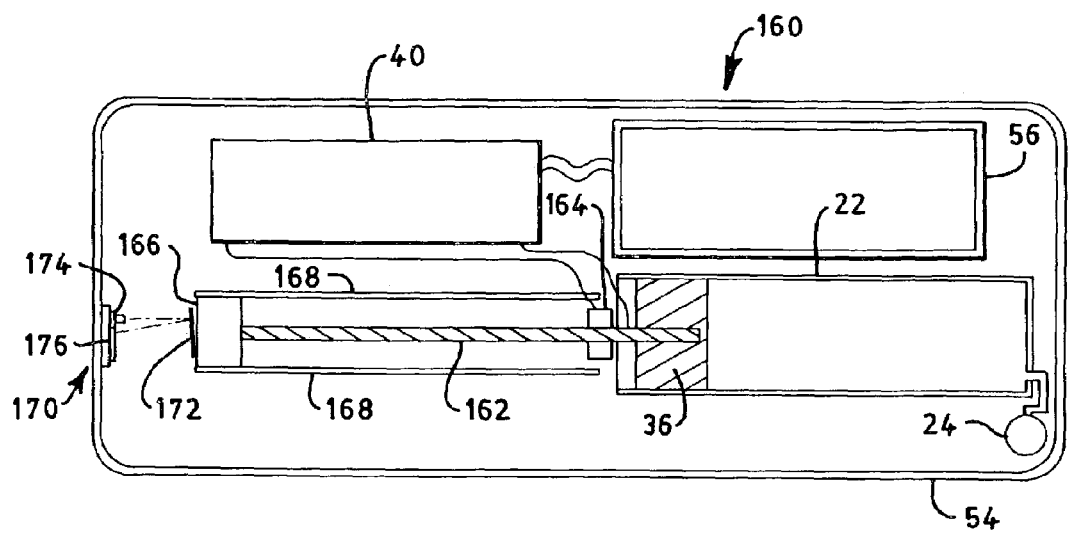
FIGS. 16 and 17 are schematic illustrations of another exemplary embodiment of a fluid delivery device constructed in accordance with the present invention, and illustrating operation of a lead screw assembly and motion sensor assemblies of the fluid delivery device.
Figure 17:
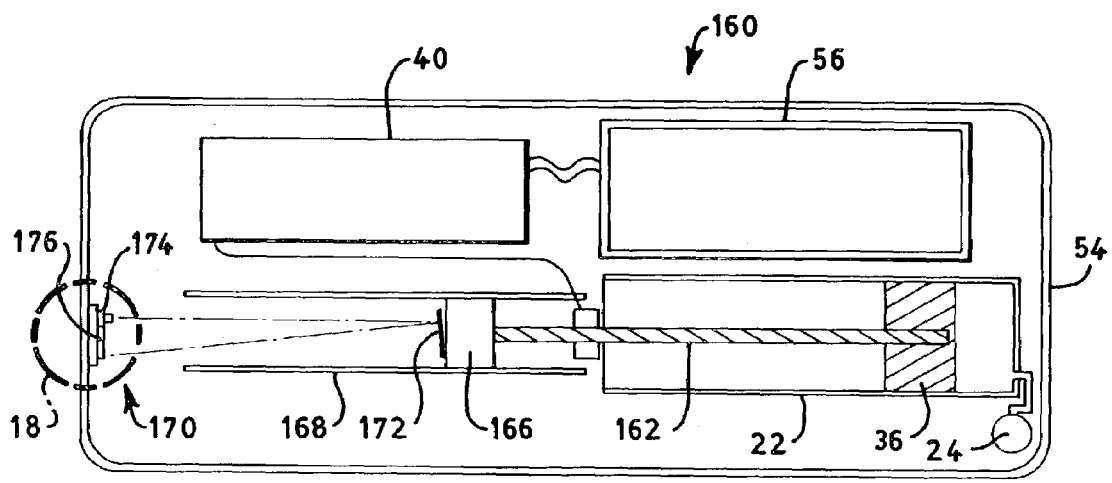

FIGS. 16 and 17 show another fluid delivery device 160 constructed in accordance with the present invention. The fluid delivery device 160 is generally similar to the fluid delivery device 10 of FIG. 3 such that similar elements have the same reference numerals. The fluid delivery device 160 of FIGS. 16 and 17, however, includes a lead screw 162 extending through a fixed, non-rotatable nut 164, and a rotary motor 166 mated to a proximal end of the lead screw 162 for causing rotation of the lead screw relative to the motor. A longitudinal guide 168 extends parallel with the lead screw 162 and receives the motor 166. The guide 168 allows longitudinal movement of the motor 166 and prevents rotation of the motor, so that actuation of the motor causes longitudinal movement of the lead screw 162 through the fixed nut 164. In the exemplary embodiment shown, the rotary motor 166 and the longitudinal guide 168 have non-circular cross-sections preventing rotation of the motor with respect to the guide.

Figure 18:
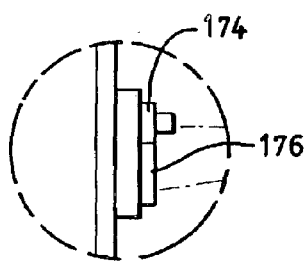
FIG. 18 is an enlarged view of a light emitter/detector of the motion sensor assembly of the fluid delivery device of FIGS. 16 and 17, as contained in circle 18 of FIG. 17.

The device 160 also includes a sensor assembly 170 having a reflector 172 secured to the lead screw 162 for longitudinal movement therewith (i.e. longitudinally moves in an amount the same as or related to the lead screw motion), and at least one light emitter 174 fixed with respect to the lead screw and directed longitudinally at the reflector 172, and at least one light detector 176 fixed with respect to the lead screw 162 and directed longitudinally at the reflector 172. An enlarged view of the light emitter 174 and the light detector 176 is shown in FIG. 18. As shown in FIGS. 16 and 17, the reflector 172 is oriented at an angle with respect to the guide 168 of the motor 166. In addition, the reflector 172 is secured to the lead screw 162 through the motor 166. Alternatively, the motor 166 can perform the function of the reflector 172, thereby eliminating one or more parts.

The processor 40 of the fluid delivery device 160 is connected to the light emitter 174 and the light detector 176 and is programmed to determine a longitudinal distance of the reflector 172 from the light emitter 174 based upon a lateral distance between a beam of light directed from the light emitter 174 to the reflector 172 and the beam of light as received by the light detector 176 from the reflector. As shown in FIGS. 16 and 17, the lateral distance increases as the longitudinal distance increases. The longitudinal distance may be based on one or more parameters such as the amount, or intensity, of light detected, or other parameters related to other properties of light, such as angle of incidence, quantities or properties of the different components of (white) light, etc. Also, in a preferred embodiment, the system provides a gross estimation of longitudinal position, but also provides a much finer resolution on relative motion since it is easier to measure a change in linear position versus a change in absolute position of the lead screw.

Figure 19:
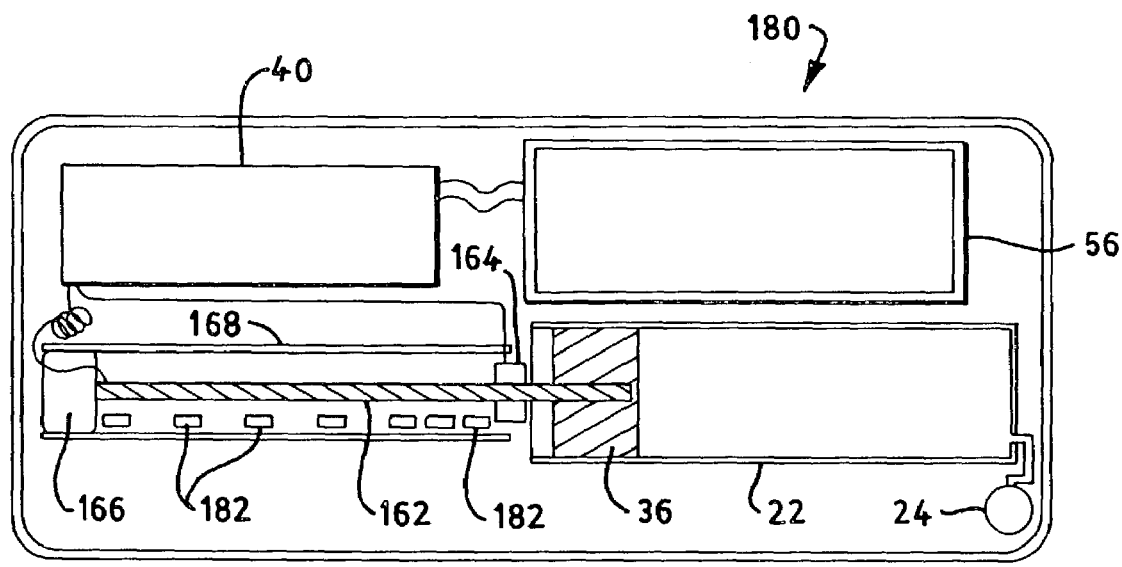
FIG. 19 is a schematic illustration of a further exemplary embodiment of a fluid delivery device constructed in accordance with the present invention, and including a lead screw assembly and motion sensor assemblies.

FIG. 19 shows another fluid delivery device 180 constructed in accordance with the present invention. The fluid delivery device 180 is similar to the fluid delivery device 160 of FIGS. 16 and 17 such that similar elements have the same reference numerals. The fluid delivery device 180 of FIG. 19, however, includes a sensor assembly including at least one light emitter/detector 182 directed laterally within the longitudinal guide 168. One of guide 168 and the motor 166 is relatively light reflective. In the exemplary embodiment shown, the motor 166 is relatively reflective and the device 180 includes a plurality of the light emitter/detectors 182 spaced longitudinally within the guide 168.

In the exemplary embodiments 160, 180 of FIGS. 16, 17 and 19, the lead screw 162 is made from electrically resistive, or other semi-conductive property material and the fixed nut 164 is made from electrically conductive, or other semi-conductive property material. The processor 40 is connected to the nut 164 and the lead screw 162 and programmed to detect an electrical signal between the nut and the lead screw. The processor 40 is further programmed to determine a relative position between the nut 164 and the lead screw 162 based on one of the electrical signal and changes to the electrical signal. In this manner, the lead screw 162 and the nut 164 can be used as another sensor assembly for monitoring the longitudinal position of the lead screw 162.

Figure 21:
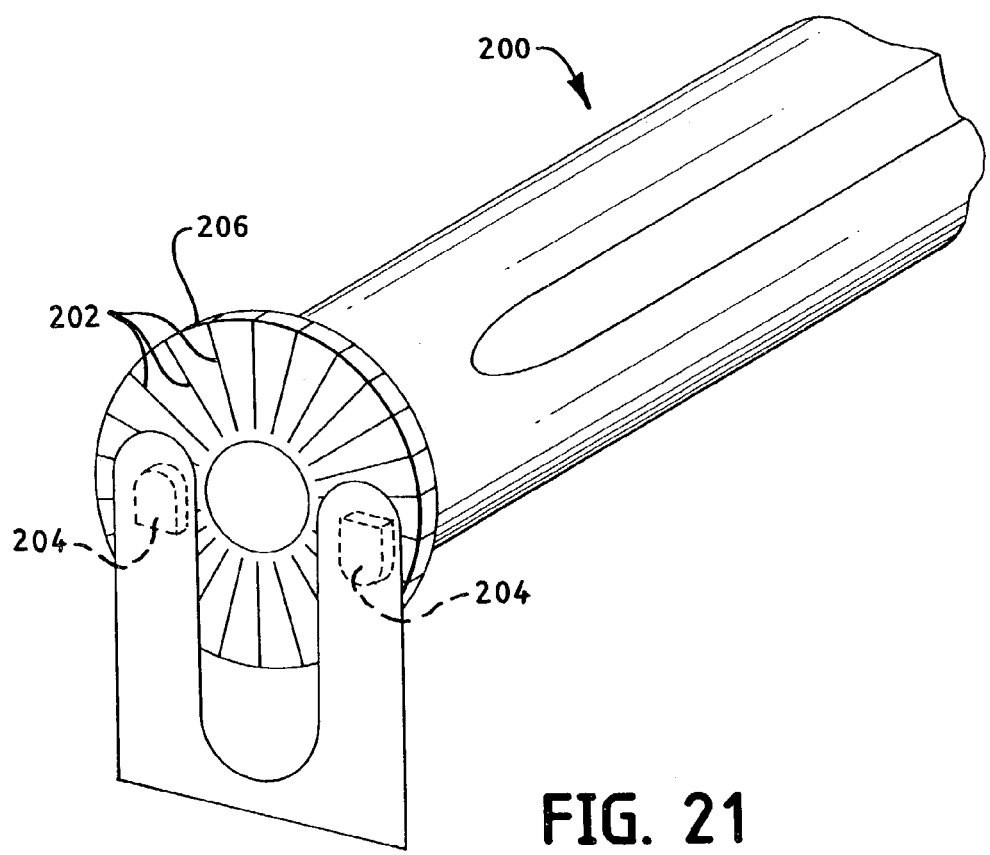
FIG. 21 is an end perspective view of a portion of another exemplary embodiment of a lead screw assembly constructed in accordance with the present invention, for use with a fluid delivery device such as the fluid delivery device of FIG. 3.
Figure 22:
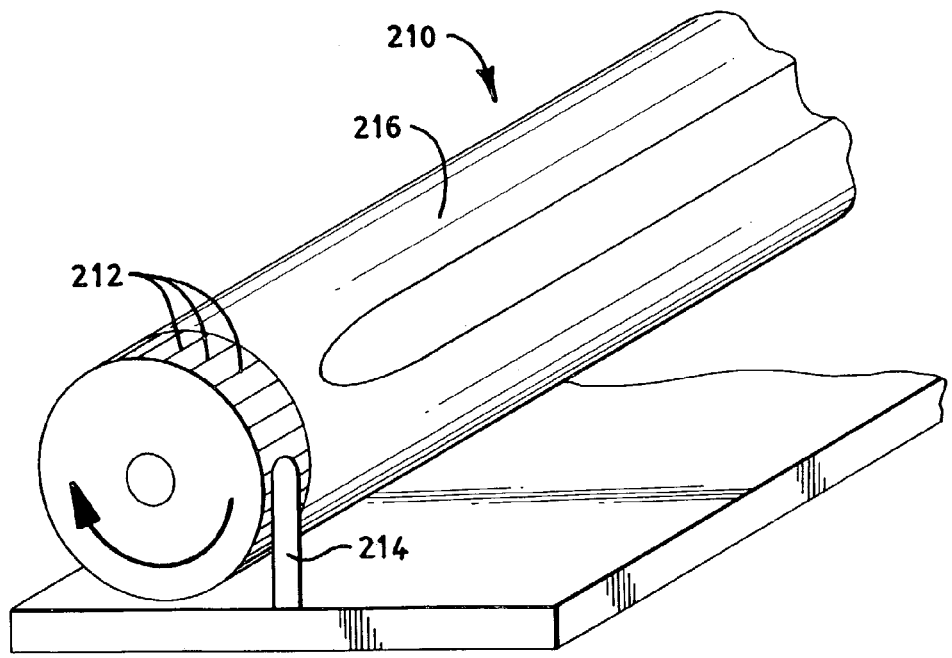
FIG. 22 is an end perspective view of a portion of a further exemplary embodiment of a lead screw assembly constructed in accordance with the present invention, for use with a fluid delivery device such as the fluid delivery device of FIG. 3.

FIGS. 21 and 22 show exemplary embodiments of tubes 200, 210, respectively, for use as part of lead screw assemblies similar to the lead screw assembly 12 of FIGS. 3, 4 and 5. The tubes 200, 210 are similar to the tube 44 of FIGS. 3, 4 and 5, but further include teeth 202, 212 secured to the tubes 200, 210. As shown in FIGS. 21 and 22, pawls 204, 214 are arranged to engage the teeth 202, 212 of the tubes 200, 210 and allow rotation of the tubes in a single direction. In the exemplary embodiment of FIG. 21, the teeth 202 of the tube 200 are radially arranged on an end wall 206 of the tube. In the exemplary embodiment of FIG. 22, the teeth 212 of the tube 210 are circumferentially arranged on a side wall 216 of the tube. Preferably, the teeth 202, 212 of the tubes 200, 210 are unitarily formed as a single piece with the tubes. For example, the teeth 202, 212 of the tubes 200, 210 are molded as part of the tubes if the tubes are made from plastic.

Figure 23:
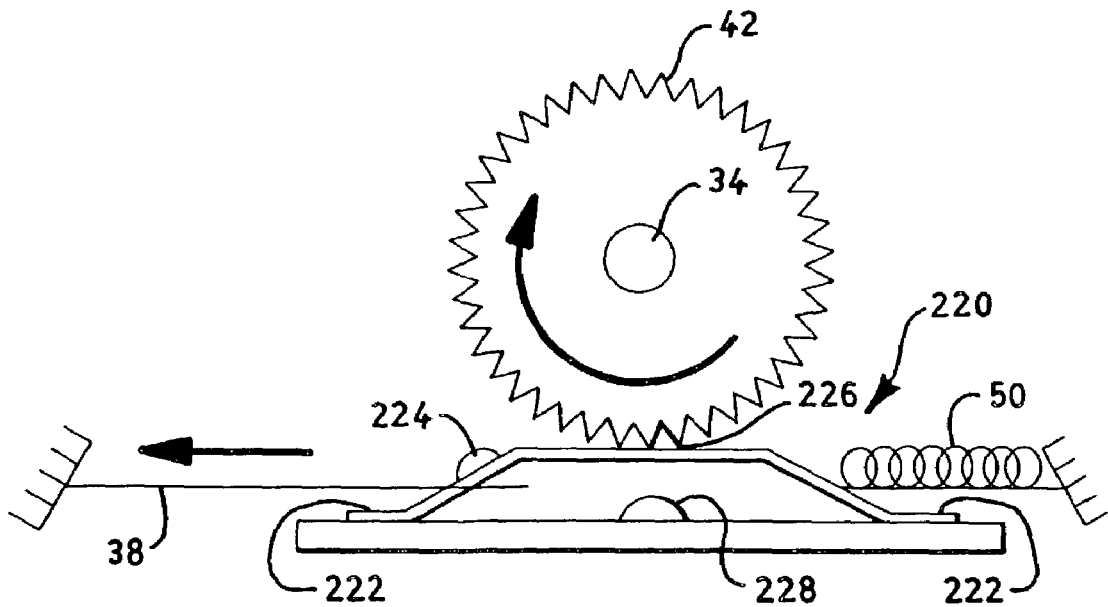
FIG. 23 is an end elevation view of another exemplary embodiment of a ratchet member constructed in accordance with the present invention, for turning a lead screw of a fluid delivery device such as the fluid delivery device of FIG. 3.

Another exemplary embodiment of a ratchet member 220 constructed in accordance with the present invention is shown in FIG. 23. The ratchet member 220 of FIG. 23 operates similar to the ratchet member 14 of FIGS. 7a and 7b to turn the gear 42 and the lead screw 34 and advance the plunger in the reservoir. The ratchet member 220 of FIG. 23, however, includes spaced-apart feet 222 movable in first and second opposing directions with respect to the gear 42, a resiliently flexible arch 224 extending between the spaced-apart sliding feet 222 and towards the gear 42, and a ratchet 226 extending from the arch 224 and engaging teeth of the gear 42 such that movement of the ratchet member 220 in the first direction with respect to the gear causes rotation of the gear while movement of the ratchet member in the second direction with respect to the gear causes no rotation of the gear and causes deflection of the arch 224 away from the gear. The ratchet member 220 is linearly moveable in the first and the second opposing directions.

An elongated shape memory element 38 is secured to the ratchet member 220. The elongated shape memory element 38 has a changeable length decreasing from an uncharged length to a charged length when at least one charge is applied to the shape memory element. The shape memory element 38 is secured to the ratchet member 220 such that the changeable length of the shape memory element decreasing from an uncharged length to a charged length causes movement of the ratchet member in one of the first and the second directions. In the exemplary embodiment of FIG. 23, the shape memory element 38 is arranged so that the changeable length of the shape memory element decreasing from an uncharged length to a charged length causes movement of the ratchet member 220 in the first direction. The ratchet member 220 is biased in the second direction by a ratchet spring 50.

A switch 228 is positioned with respect to the arch 224 of the ratchet member 220 such that the arch 224 contacts the switch 228 upon deflection of the arch away from the gear 42 during movement of the ratchet member 220 in the second direction with respect to the gear 42. The switch 228 provides a signal upon being contacted by the arch 224 of the ratchet member 220, and is connected to the processor of the fluid delivery. The processor, in turn, is programmed to determine that the gear 42 has been adequately rotated upon receiving a signal from the switch 228.

Figure 24:
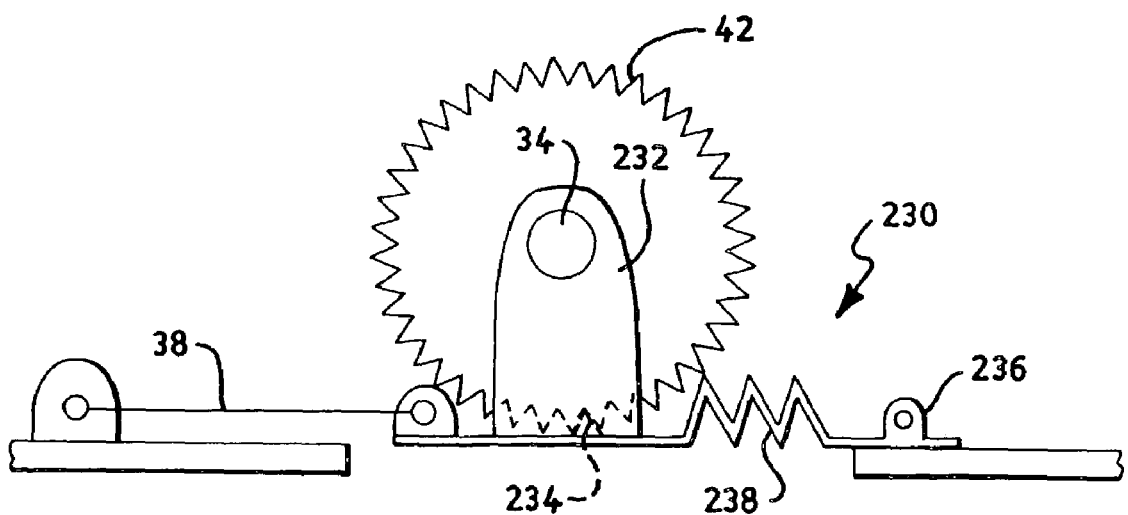
FIG. 24 is an end elevation view of a further exemplary embodiment of a ratchet member constructed in accordance with the present invention, for turning a lead screw of a fluid delivery device such as the fluid delivery device of FIG. 3.

A further exemplary embodiment of a ratchet member 230 constructed in accordance with the present invention is shown in FIG. 24. The ratchet member 230 includes arms 232 pivotally secured on the lead screw 34 on opposite sides of the gear 42, and a ratchet 234 engaging teeth of the gear 42 such that pivotal movement of the ratchet member 230 about the lead screw 34 in a first direction causes rotation of the gear 42 while pivotal movement of the ratchet member 230 about the lead screw 34 in a second direction causes no rotation of the gear. In the exemplary embodiment shown, the ratchet member 230 also includes an anchor 236 fixed in position with respect to the gear 42, and a spring 238 biasing the ratchet 234 in the second direction and towards the anchor 236.

Additional exemplary embodiments of a threaded lead screw 250, a threaded gear 252, a plunger 254 and a reservoir 256 constructed in accordance with the present invention are shown in FIGS. 25 and 26. The reservoir 256 includes a cylindrical side wall 258 extending towards an outlet 260, and the lead screw 250 is received in the reservoir 256 and extends towards the outlet 260 generally parallel with the side wall 258 of the reservoir 256, and the plunger 254 is secured to an end of the lead screw 250. The lead screw 250, the plunger 254 and the reservoir 256 are adapted such that a fluid-tight seal is formed between the plunger 254 and the lead screw 250 and a fluid-tight seal is formed between the plunger 254 and the side wall 258 of the reservoir 256, so that movement of the plunger 254 towards the outlet 260 of the reservoir 256 forces fluid through the outlet. The gear 252 is rotatably and threadedly received on the lead screw 250.

The lead screw 250 includes one of a longitudinal extending groove 262 and a laterally extending pin 264, and a housing 266 containing the reservoir 256, the lead screw 250 and the plunger 254 includes the other of the longitudinal extending groove 262 and the laterally extending pin 264. The laterally extending pin 264 is slidingly received within the longitudinally extending groove 262 to allow longitudinal advancement of the lead screw 250 and prevent rotation of the lead screw 250, so that rotation of the gear 252 causes longitudinally movement of the lead screw 250 and the plunger 254 within the reservoir 256.

In the exemplary embodiment of FIGS. 25 and 26, the lead screw 250 includes the longitudinally extending groove 262 and the housing 266 includes the laterally extending pin 264. In the exemplary embodiment of FIG. 27, a lead screw 268 includes two longitudinally extending grooves 262 and the housing 266 includes two laterally extending pins 264, with one pin 264 received in each groove 262.

Figure 28:
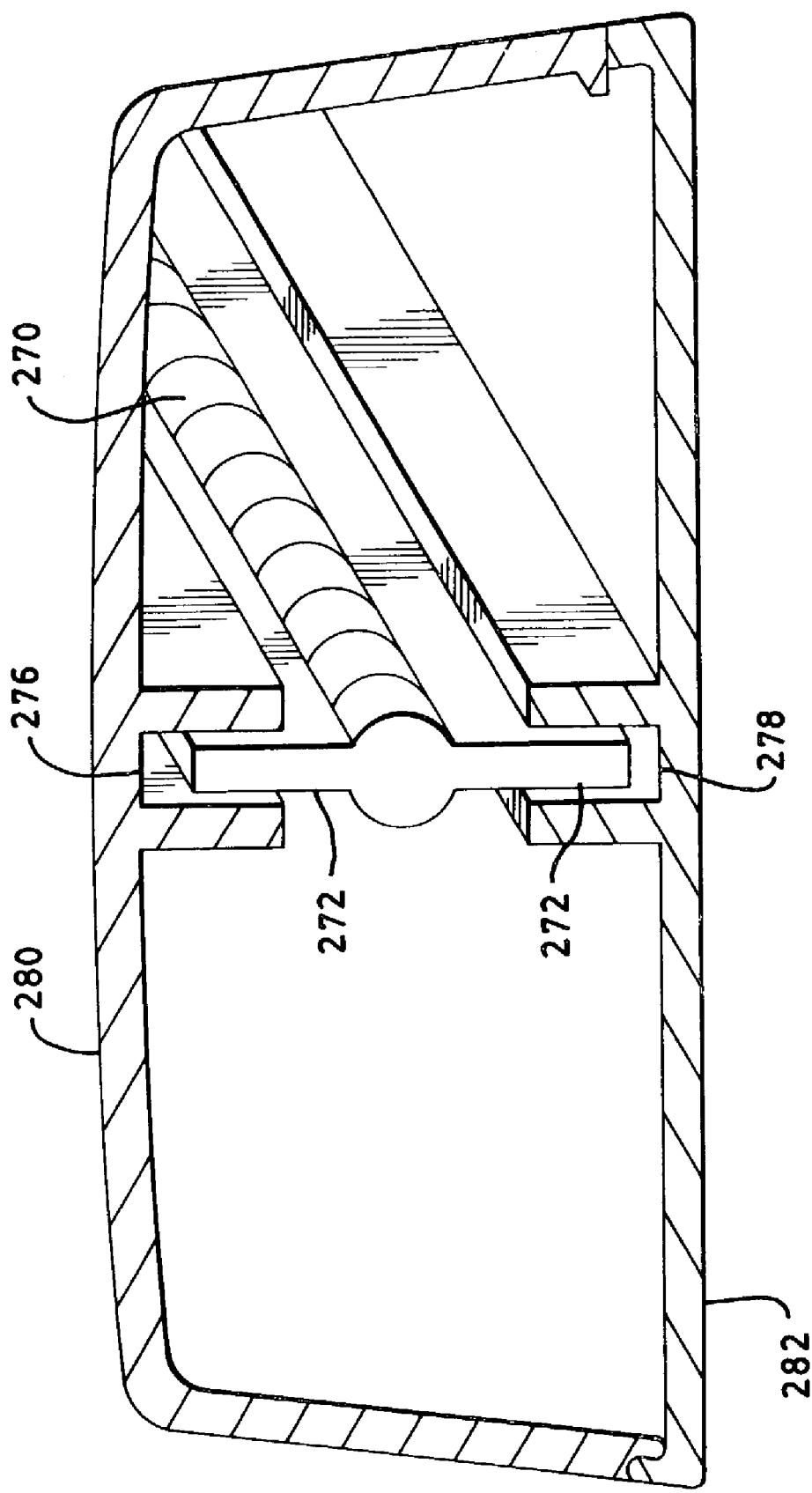
FIG. 28 is an end perspective view of an additional exemplary embodiment of a lead screw and corresponding housing portions constructed in accordance with the present invention.

In the exemplary embodiment of FIG. 28, a lead screw 270 includes two laterally extending pins 272 and a housing 274 includes two longitudinally extending grooves 276, 278. The longitudinally extending grooves 276, 278 are unitarily formed as part of upper and lower portions 280, 282 of the housing 274.

As illustrated by the above described exemplary embodiments, the present invention generally provides new and improved dispenser components for a device for delivering fluid, such as insulin for example, to a patient. It should be understood that the embodiments described herein are merely exemplary and that a person skilled in the art may make variations and modifications to the embodiments described without departing from the spirit and scope of the present invention. All such equivalent variations and modifications are intended to be included within the scope of this invention as defined by the appended claims.

What is claimed is:

1. A device for delivering fluid to a patient, comprising:
    an exit port assembly;
    a reservoir including a side wall extending towards an outlet connected to the exit port assembly;
    a threaded lead screw received at least partly in the reservoir and longitudinally extending towards the outlet;
    a plunger secured to the lead screw and having an outer periphery linearly slideable along the side wall of the reservoir;
    a tube coaxially received on the lead screw and including a longitudinal slot;
    a pin extending through the lead screw and the slot of the tube; and
    a gear secured to the tube for rotation therewith.

2. A device according to claim 1, further comprising:
    a reference element secured to the pin;
    at least one light emitter directed laterally at the tube for directing a beam of light at the tube;
    at least one light detector directed laterally at the tube for receiving the beam of light reflected away from the tube;
    wherein one of the tube and the reference element has a light reflective outer surface.

3. A device according to claim 2, wherein the reference element has a light reflective outer surface.

4. A device according to claim 2, wherein the reference element is annular and coaxially received for sliding movement along an outer surface of the tube.

5. A device according to claim 1, wherein the lead screw extends through and is threadedly received within a non-rotating nut assembly.

6. A device according to claim 5, wherein the non-rotating nut assembly comprises:
    at least two laterally movable threaded inserts including threaded surfaces for threadedly receiving the lead screw upon being biased laterally inwardly against the lead screw;
    a spring biasing the threaded inserts laterally inwardly against the lead screw; and
    at least one spacer cam movable between a first position preventing the threaded inserts from being biased laterally inwardly against the lead screw and a second position allowing the threaded inserts to be biased laterally inwardly against the lead screw.

7. A device according to claim 6, wherein, in the first position, the spacer cam is positioned between the threaded inserts.

8. A device according to claim 6, wherein the spacer cam is laterally movable with respect to the lead screw.

9. A device according to claim 6, wherein the spacer cam is operatively connected to the gear such that rotation of the gear causes movement of the spacer cam to the second position.

10. A device according to claim 6, further comprising:
    a gear cam operatively connected with the gear for rotation with the gear about the lead screw;
    a spacer follower laterally moveable with respect to the lead screw and connected to the spacer cam such that lateral movement of the spacer follower in a first direction with respect to the lead screw causes movement of the spacer cam to the second position, wherein the spacer follower is received against the gear cam and the gear cam and the spacer follower are shaped such that rotation of the gear cam about the lead screw causes lateral movement of the spacer follower in the first direction with respect to the lead screw.

11. A device according to claim 10, wherein the spacer follower and the spacer cam are connected through a spacer ring coaxially positioned with respect to the lead screw.

12. A device according to claim 10, wherein the gear cam is provided as part of a gear ring coaxially positioned with respect to the lead screw and including at least one spline extending into a keyway of the gear.

13. A device according to claim 12, wherein the gear cam is formed in a radially outwardly facing surface of the spline.

14. A device according to claim 12, wherein the gear ring includes a latch allowing the spacer follower to exit the gear cam and preventing the spacer follower from re-entering the gear cam.

15. A device according to claim 1, further comprising a set of at least two pawls, wherein each pawl engages teeth of the gear and allows rotation of the gear in a single direction.

16. A device according to claim 1, further comprising a ratchet member movable with respect to the gear and including a ratchet engaging teeth of the gear such that movement of the ratchet in a first direction causes rotation of the gear while movement of the ratchet in a second direction causes no rotation of the gear.

17. A device according to claim 16, further comprising an elongated shape memory element having a changeable length decreasing from an uncharged length to a charged length when at least one charge is applied to the shape memory element, wherein the shape memory element is secured to the ratchet member such that the changeable length of the shape memory element decreasing from an uncharged length to a charged length causes movement of the ratchet in one of the first and the second directions.

18. A device according to claim 17, wherein the changeable length of the shape memory element decreasing from an uncharged length to a charged length causes movement of the ratchet in the first direction.

19. A device according to claim 18, wherein the ratchet is biased in the second direction by a ratchet spring.

20. A device according to claim 19, wherein the ratchet spring comprises a hinge spring.

21. A device according to claim 16, wherein the ratchet is linearly moveable in the first and the second directions.

22. A device according to claim 16, wherein the ratchet member comprises:
an anchor fixed in position with respect to the gear; and
a spring biasing the ratchet in the second direction and away from the anchor.

23. A device according to claim 1, further comprising a sensor detecting linear movement of the lead screw.

24. A device according to claim 23, further comprising:
a non-rotating nut fixed with respect to the reservoir and threadedly receiving the lead screw therethrough so that rotation of the lead screw causes linear movement of the lead screw with respect to the nut;
a ratchet operatively arranged with respect to the gear such that movement of the ratchet in a first direction causes rotation of the gear while movement of the ratchet in a second direction causes no rotation of the gear;
an elongated shape memory element having a changeable length decreasing from an uncharged length to a charged length when at least one charge is applied to the shape memory element, wherein the shape memory element is secured to the ratchet member such that the changeable length of the shape memory element decreasing from an uncharged length to a charged length causes movement of the ratchet in one of the first and the second directions; and
a processor connected to the shape memory element and the sensor detecting linear movement of the lead screw, and programmed to apply a charge to the shape memory element and remove the charge upon receiving a signal from the sensor indicative of linear movement of the lead screw.

25. A device according to claim 1, further comprising a ratchet engaging teeth of the gear such that movement of the ratchet in a first direction causes rotation of the gear while movement of the ratchet in a second direction causes no rotation of the gear, a first electrical lead connected to the gear, and a second electrical lead connected to the ratchet, and wherein the gear and the ratchet are made from electrically conductive material.

26. A device according to claim 25, further comprising a processor connected to the first and second electrical leads and programmed to determine whether the gear has rotated based at least in part on electrical discontinuities between the ratchet and the gear.

27. A device according to claim 25, further comprising at least one pawl allowing rotation of the gear in a single direction and a third electrical lead connected to the pawl, and wherein the pawl is made from electrically conductive material.

28. A device according to claim 27, further comprising a processor connected to the first, the second and the third electrical leads and programmed to determine whether the gear has rotated based at least in part on electrical discontinuities between the ratchet, the pawl and the gear.

29. A device according to claim 25, further comprising:
an elongated shape memory element having a changeable length decreasing from an uncharged length to a charged length when at least one charge is applied to the shape memory element, wherein the shape memory element is secured to the ratchet such that the changeable length of the shape memory element decreasing from an uncharged length to a charged length causes movement of the ratchet in one of the first and the second directions; and
a processor connected to the shape memory element and the first and second electrical leads, and programmed to,
apply a charge to the shape memory element in order to cause rotation of the gear,
determine whether the gear has been rotated based at least in part on electrical discontinuities between the ratchet and the gear, and
remove the charge from the shape memory element upon determining that the gear has been rotated.

30. A device according to claim 1, further comprising an electrically conductive brush biased against a face of the gear, and wherein the face of the gear includes radially spaced bumps thereon, and wherein one of the face and the bumps are electrically conductive.

31. A device according to claim 30, further comprising a processor connected to the brush and one of the face and the bumps of the gear, and programmed to determine whether the gear has rotated based at least in part on electrical discontinuities between the brush and the gear.

32. A device according to claim 30, wherein the bumps of the gear correspond to outer circumferential teeth of the gear.

33. A device according to claim 1, further comprising:
an encoder disk coaxially secured to the tube and including radially spaced light reflective indicia thereon;
a light emitter directed at the encoder disk; and
a light detector directed at the encoder disk.

34. A device according to claim 33, wherein the radially spaced light reflective indicia is located on an outer circumferential surface of the encoder disk.

35. A device according to claim 33, wherein the encoder disk is secured to the gear.

36. A device according to claim 33, wherein the encoder disk has a recess on a face thereof.

37. A device according to claim 1, further comprising:
a reference element secured to the pin for longitudinal movement along an outer surface of the tube;
at least one light emitter directed laterally at the outer surface of the tube; and
at least one light detector directed laterally at the outer surface of the tube;
wherein one of the outer surface of the tube and the reference element is relatively light reflective; and
wherein the encoder disk includes a recess on a face thereof to receive the reference element.

38. A device according to claim 37, wherein the reference element has a light reflective outer surface.

39. A device according to claim 37, wherein the reference element is annular and coaxially received for sliding movement along an outer surface of the tube.

40. A device according to claim 1, further comprising:
a rotary motor mated to a proximal end of the lead screw for causing rotation of the lead screw relative to the motor; and
a longitudinal guide extending parallel with the lead screw and receiving the motor, wherein the guide allows longitudinal movement of the motor and prevents rotation of the motor.

41. A device according to claim 40, wherein the rotary motor and the longitudinal guide have non-circular cross-sections preventing rotation of the motor with respect to the guide.

42. A device according to claim 40, further comprising:
a reflector secured to the motor;
at least one light emitter fixed with respect to the motor and directed longitudinally at the reflector; and
at least one light detector fixed with respect to the motor and directed longitudinally at the reflector.

43. A device according to claim 42, wherein the reflector is oriented at an angle with respect to the guide of the motor.

44. A device according to claim 42, further comprising a processor connected to the light emitter and the light detector and programmed to determine a longitudinal distance of the reflector from the light emitter based upon a lateral distance between a beam of light directed from the light emitter to the reflector and the beam of light as received by the light detector from the reflector.

45. A device according to claim 40, further comprising:
at least one light emitter directed laterally within the longitudinal guide; and
at least one light detector directed laterally within the longitudinal guide;
wherein one of guide and the motor is relatively light reflective.

46. A device according to claim 45, wherein the motor is relatively reflective.

47. A device according to claim 45, comprising a plurality of the light emitters and light detectors spaced longitudinally within the guide.

48. A device according to claim 1, wherein the lead screw is made from electrically resistive material and extends through and is threadedly received within a non-rotating longitudinally fixed nut made from electrically conductive material.

49. A device according to claim 48, further comprising a processor connected to the nut and the lead screw and programmed to detect an electrical signal between the nut and the lead screw.

50. A device according to claim 49, wherein the processor is further programmed to determine a relative position between the nut and the lead screw based on one of the electrical signal and changes to the electrical signal.

51. A device according to claim 1, further comprising teeth secured to the tube and a pawl engaging the teeth of the tube and allowing rotation of the tube in a single direction.

52. A device according to claim 50, wherein the teeth of the tube are radially arranged on an end wall of the tube.

53. A device according to claim 50, wherein the teeth of the tube are circumferentially arranged on a side wall of the tube.

54. A device according to claim 50, wherein the teeth of the tube are unitarily formed as a single piece with the tube.

55. A device according to claim 43, wherein the teeth of the tube are molded as part of the tube.

56. A device according to claim 1, further comprising:
a ratchet member including,
spaced-apart feet movable in first and second opposing directions with respect to the gear,
a resiliently flexible arch extending between the spaced-apart sliding feet and towards the gear,
a ratchet extending from the arch and engaging teeth of the gear such that movement of the ratchet member in the first direction with respect to the gear causes rotation of the gear while movement of the ratchet member in the second direction with respect to the gear causes no rotation of the gear and causes deflection of the arch away from the gear; and
a switch positioned with respect to the arch of the ratchet member such that the arch contacts the switch upon deflection of the arch away from the gear during movement of the ratchet member in the second direction with respect to the gear.

57. A device according to claim 56, further comprising an elongated shape memory element having a changeable length decreasing from an uncharged length to a charged length when at least one charge is applied to the shape memory element, wherein the shape memory element is secured to the ratchet member such that the changeable length of the shape memory element decreasing from an uncharged length to a charged length causes movement of the ratchet in one of the first and the second directions.

58. A device according to claim 56, wherein the changeable length of the shape memory element decreasing from an uncharged length to a charged length causes movement of the ratchet member in the first direction.

59. A device according to claim 57, wherein the ratchet member is biased in the second direction by a ratchet spring.

60. A device according to claim 56, wherein the ratchet member is linearly moveable in the first and the second directions.

61. A device according to claim 1, further comprising a ratchet member including arms pivotally secured on the tube on opposite sides of the gear and including a ratchet engaging teeth of the gear such that pivotal movement of the ratchet member about the tube in a first direction causes rotation of the gear while pivotal movement of the ratchet member about the tube in a second direction causes no rotation of the gear.

62. A device according to claim 61, wherein the ratchet member comprises:
an anchor fixed in position with respect to the gear; and a spring biasing the ratchet member in the second direction and towards the anchor.

63. A device according to claim 61, further comprising an elongated shape memory element having a changeable length decreasing from an uncharged length to a charged length when at least one charge is applied to the shape memory element, wherein the shape memory element is secured to the ratchet member such that the changeable length of the shape memory element decreasing from an uncharged length to a charged length causes pivotal movement of the ratchet in one of the first and the second directions.

64. A device according to claim 63, wherein the changeable length of the shape memory element decreasing from an uncharged length to a charged length causes pivotal movement of the ratchet in the first direction.

65. A device according to claim 1, wherein the plunger is non-rotatable with respect to the side wall of the reservoir.

66. A device according to claim 65, wherein the side wall of the reservoir and the plunger each have a non-circular cross-section.

67. A device according to claim 1, wherein the reservoir contains a therapeutic fluid.

68. A device according to claim 67, wherein the therapeutic fluid is insulin.

69. A device according to claim 1, wherein the exit port assembly includes a transcutaneous patient access tool.

70. A device according to claim 69, wherein the transcutaneous patient access tool comprises a needle.

71. A device for delivering fluid to a patient, comprising:
an exit port assembly;
a reservoir including a side wall extending towards an outlet connected to the exit port assembly;
a threaded lead screw received at least partly in the reservoir and longitudinally extending towards the outlet;
a plunger secured to the lead screw and having an outer periphery linearly slideable along the side wall of the reservoir;
a gear radially extending from the lead screw, wherein the gear and the lead screw are operatively connected such that rotation of the gear about the lead screw causes longitudinally movement of the lead screw towards the outlet of the reservoir; and
a ratchet member including arms pivotally secured on the lead screw on opposite sides of the gear and including a ratchet engaging teeth of the gear such that pivotal movement of the ratchet member about the lead screw in a first direction causes rotation of the gear while pivotal movement of the ratchet member about the lead screw in a second direction causes no rotation of the gear.

72. A device according to claim 71, wherein the ratchet member comprises:
an anchor fixed in position with respect to the gear; and
a spring biasing the ratchet in the second direction and towards the anchor.

73. A device according to claim 71, further comprising an elongated shape memory element having a changeable length decreasing from an uncharged length to a charged length when at least one charge is applied to the shape memory element, wherein the shape memoiy element is secured to the ratchet member such that the changeable length of the shape memory element decreasing from an uncharged length to a charged length causes pivotal movement of the ratchet in one of the first and the second directions.

74. A device according to claim 73, wherein the changeable length of the shape memory element decreasing from an uncharged length to a charged length causes pivotal movement of the ratchet in the first direction.

75. A device according to claim 71, wherein the reservoir contains a therapeutic. fluid.

76. A deVice according to claim 75, wherein the therapeutic fluid is insulin.

77. A device according to claim 71, wherein the exit port assembly includes a transcutaneous patient access tool.

78. A device according to claim 77, wherein the transcutaneous patient access tool comprises a needle.

79. A device for delivering fluid to a patient, comprising:
an exit port assembly;
a reservoir including a side wall extending towards an outlet connected to the exit port assembly;
a threaded lead screw received at least partly in the reservoir and longitudinally extending towards the outlet;
a plunger secured to the lead screw and having an outer periphery linearly slideable along the side wall of the reservoir;
a gear radially extending from the lead screw, wherein the gear and the lead screw are operatively coniiected such that rotation of the gear about the lead screw causes longitudinally movement of the lead screw towards the outlet of the reservoir; and
a ratchet member including,
spaced-apart feet movable in first and second opposing directions with respect to the gear,
a resiliently flexible arch extending between the spaced-apart feet and towards the gear,
a ratchet extending from the arch and engaging teeth of the gear such that movement of the ratchet member in the first direction causes rotation of the gear while movement of the ratchet member in the second direction with respect to the gear causes no rotation of the gear and causes deflection of the arch away from the gear.

80. A device according to claim 79, further comprising a switch positioned with respect to the arch of the ratchet member such that the arch contacts the switch upon deflection of the arch away from the gear.

81. A device according to claim 79, further comprising an elongated shape memory element having a changeable length decreasing from an uncharged length to a charged length when at least one charge is applied to the shape memory element, wherein the shape memory element is secured to the ratchet member such that the changeable length of the shape memory element decreasing from an uncharged length to a charged length causes movement of the ratchet member in one of the first and the second directions.

82. A device according to claim 81, wherein the changeable length of the shape memory element decreasing from an uncharged length to a charged length causes movement of the ratchet member in the first direction.

83. A device according to claim 79, wherein the ratchet member is biased in the second direction by a ratchet spring.

84. A device according to claim 79, wherein the ratchet member is linearly moveable in the first and the second directions.

85. A device according to claim 79, wherein the reservoir contains a therapeutic fluid.

86. A device according to claim 85, wherein the therapeutic fluid is insulin.

87. A device according to claim 79, wherein the exit port assembly includes a transcutaneous patient access tool.

88. A device according to claim 87, wherein the transcutaneous patient access tool comprises a needle.

89. A device for delivering fluid to a patient, comprising:
an exit port assembly;
a reservoir including a side wall extending towards an outlet connected to the exit port assembly;
a threaded lead screw received at least partly in the reservoir and longitudinally extending towards the outlet;
a plunger secured to the lead screw and having an outer periphery linearly slideable along the side wall of the reservoir;
a gear radially extending from the lead screw, wherein the gear and the lead screw are operatively connected such that rotation of the gear causes longitudinally movement of the lead screw towards the outlet of the reservoir; and
a ratchet member including,
an anchor fixed in position with respect to the gear,
a ratchet engaging teeth of the gear such that movement of the ratchet in a first direction causes rotation of the gear while movement of the ratchet in a second direction causes no rotation of the gear, and
a spring connecting the anchor and the ratchet and biasing the ratchet in one of the first and the second directions.

90. A device according to claim 89, wherein the anchor, the ratchet and the spring of the ratchet member comprise a unitary piece of material.

91. A device according to claim 89, further comprising an elongated shape memory element having a changeable length decreasing from an uncharged length to a charged length when at least one charge is applied to the shape memory element, wherein the shape memory element is secured to the ratchet member such that the changeable length of the shape memory element decreasing from an uncharged length to a charged length causes movement of the ratchet member in one of the first and the second directions.

92. A device according to claim 91, wherein the changeable length of the shape memory element decreasing from an uncharged length to a charged length causes movement of the ratchet member in the first direction.

93. A device according to claim 89, wherein the ratchet is biased in the second direction by the spring.

94. A device according to claim 93, wherein the ratchet is biased in the second direction by a second spring.

95. A device according to claim 94, wherein the second spring comprises a hinge spring.

96. A device according to claim 89, wherein the ratchet is linearly moveable in the first and the second directions.

97. A device according to claim 89, wherein the reservoir contains a therapeutic fluid.

98. A device according to claim 97, wherein the therapeutic fluid is insulin.

99. A device according to claim 89, wherein the exit port assembly includes a transcutaneous patient access tool.

100. A device according to claim 99, wherein the transcutaneous patient access tool comprises a needle.

101. A device for delivering fluid to a patient, comprising:
an exit port assembly;
a reservoir including a side wall extending towards an outlet connected to the exit port assembly;
a threaded lead screw received at least partly in the reservoir and longitudinally extending towards the outlet;
a plunger secured to the lead screw and having an outer periphery linearly slideable along the side wall of the reservoir;
a gear radially extending from the lead screw, wherein the gear and the lead screw are operatively connected such that rotation of the gear causes longitudinally movement of the lead screw towards the outlet of the reservoir, wherein a face of the gear includes radially spaced bumps thereon, and one of the face and the bumps are electrically conductive; and
an electrically conductive brush biased against the face of the gear.

102. A device according to claim 101, further comprising a processor connected to the brush and one of the face and the bumps of the gear, and programmed to determine whether the gear has rotated based at least in part on electrical discontinuities between the brush and the gear.

103. A device according to claim 101, wherein the bumps of the gear correspond to outer circumferential teeth of the gear.

104. A device according to claim 101, wherein the reservoir contains a therapeutic fluid.

105. A device according to claim 104, wherein the therapeutic fluid is insulin.

106. A device according to claim 101, wherein the exit port assembly includes a transcutaneous patient access tool.

107. A device according to claim 106, wherein the transcutaneous patient access tool comprises a needle.

* * * * *